US011045312B2

(12) United States Patent
Flaction et al.

(10) Patent No.: US 11,045,312 B2
(45) Date of Patent: Jun. 29, 2021

(54) STENT SEALS AND METHOD OF PRODUCTION

(71) Applicant: Symetis SA, Ecublens (CH)

(72) Inventors: Lionel Flaction, Chavannes-pres-Renens (CH); Stéphane Delaloye, Bulach (CH); Youssef Biadillah, Geneva (CH); Arnaud Humair, Chatelaine (CH)

(73) Assignee: Boston Scientific Limited, Hamilton (BM)

( * ) Notice: Subject to any disclaimer, the term of this patent is extended or adjusted under 35 U.S.C. 154(b) by 366 days.

(21) Appl. No.: 15/548,354

(22) PCT Filed: Feb. 2, 2016

(86) PCT No.: PCT/EP2016/052210
§ 371 (c)(1),
(2) Date: Aug. 2, 2017

(87) PCT Pub. No.: WO2016/124615
PCT Pub. Date: Aug. 11, 2016

(65) Prior Publication Data
US 2018/0263765 A1    Sep. 20, 2018

(30) Foreign Application Priority Data

Feb. 2, 2015   (EP) ..................................... 15153525
Apr. 22, 2015  (EP) ..................................... 15164752
(Continued)

(51) Int. Cl.
*A61F 2/24*   (2006.01)
*A61F 2/06*   (2013.01)

(52) U.S. Cl.
CPC .............. *A61F 2/2412* (2013.01); *A61F 2/06* (2013.01); *A61F 2210/0061* (2013.01); *A61F 2250/0003* (2013.01)

(58) Field of Classification Search
CPC .......... A61F 2/24; A61F 2/246; A61F 2/0095; A61F 2/2418; A61F 2/2412; A61F 2/06;
(Continued)

(56) References Cited

U.S. PATENT DOCUMENTS 6,729,356 B1   5/2004   Baker et al.
9,216,076 B2  12/2015   Mitra et al.
(Continued)

FOREIGN PATENT DOCUMENTS

EP    2389136 A1   11/2011
EP    2753372 A1    7/2014
(Continued)

OTHER PUBLICATIONS

International Search Report and Written Opinion dated Aug. 8, 2016 for International Application No. PCT/EP2016/052210.

*Primary Examiner* — Alvin J Stewart
(74) *Attorney, Agent, or Firm* — Seager, Tufte & Wickhem LLP

(57) ABSTRACT

Various embodiments of a seal for a stent-valve, and methods of production, are described. In some embodiments, the seal or a skirt comprises a fabric wall portion and a polymeric material fused to the fabric wall portion, the polymeric material having a melting temperature that is lower than that of the fabric wall portion. The fibres of the fabric may remain unmelted at the interface with the polymeric material, the polymeric material being attached to material to the fibres of the fabric wall portion by fusion. The polymeric
(Continued)

material may provide a welded joint to another fabric wall portion and/or may reinforce the fabric and/or may occlude pores of the fabric.

15 Claims, 14 Drawing Sheets

(30) Foreign Application Priority Data

Jul. 10, 2015 (EP) .................................... 15176367
Sep. 28, 2015 (EP) .................................... 15187060

(58) Field of Classification Search
CPC .. A61F 2/2409; A61F 2/945; A61F 2002/077; A61F 2250/0003
See application file for complete search history.

(56) References Cited

U.S. PATENT DOCUMENTS

| | | | |
|---|---|---|---|
| 9,675,451 B2* | 6/2017 | Garde | A61F 2/2409 |
| 9,820,851 B2* | 11/2017 | Braido | A61F 2/2409 |
| 10,420,658 B2* | 9/2019 | Delaloye | A61F 2/2418 |
| 2006/0085080 A1* | 4/2006 | Bechgaard | A61L 27/44 |
| | | | 623/23.43 |
| 2007/0254158 A1 | 11/2007 | Bormann et al. | |
| 2011/0282426 A1 | 11/2011 | Mitra et al. | |
| 2012/0123529 A1* | 5/2012 | Levi | A61F 2/2412 |
| | | | 623/2.11 |
| 2013/0190857 A1 | 7/2013 | Mitra et al. | |
| 2013/0197622 A1 | 8/2013 | Mitra et al. | |
| 2013/0274873 A1 | 10/2013 | Delaloye et al. | |
| 2013/0331929 A1 | 12/2013 | Mitra et al. | |
| 2014/0039614 A1* | 2/2014 | Delaloye | A61F 2/2418 |
| | | | 623/2.36 |
| 2014/0277417 A1* | 9/2014 | Schraut | A61F 2/2403 |
| | | | 623/2.17 |
| 2015/0073545 A1* | 3/2015 | Braido | A61F 2/2412 |
| | | | 623/2.18 |
| 2015/0320556 A1* | 11/2015 | Levi | A61F 2/2427 |
| | | | 623/2.11 |
| 2016/0030165 A1* | 2/2016 | Mitra | A61F 2/2409 |
| | | | 623/2.42 |
| 2016/0106538 A1 | 4/2016 | Mitra et al. | |
| 2016/0194425 A1 | 7/2016 | Mitra et al. | |
| 2016/0354201 A1* | 12/2016 | Keogh | A61F 2/2418 |
| 2016/0361160 A1* | 12/2016 | Braido | A61F 2/2412 |
| 2017/0014229 A1* | 1/2017 | Nguyen-Thien-Nhon | A61F 2/2418 |
| 2019/0053899 A1* | 2/2019 | Levi | A61F 2/2418 |
| 2019/0133757 A1* | 5/2019 | Zhang | A61F 2/243 |
| 2019/0183666 A1* | 6/2019 | Folan | A61F 2/88 |
| 2019/0307924 A1* | 10/2019 | Stevenson | A61L 27/34 |

FOREIGN PATENT DOCUMENTS

| | | |
|---|---|---|
| EP | 2753372 A4 | 8/2015 |
| EP | 2389136 A4 | 11/2015 |
| EP | 2967862 A2 | 1/2016 |
| EP | 2967862 A4 | 5/2017 |
| JP | 2004049772 A | 2/2004 |
| WO | 2004032987 A1 | 4/2004 |
| WO | 2010083558 A1 | 7/2010 |
| WO | 2013033791 A1 | 3/2013 |
| WO | 2014072439 A1 | 5/2014 |
| WO | 2014072439 A9 | 7/2014 |
| WO | 2014140230 A1 | 9/2014 |
| WO | 2014145564 A2 | 9/2014 |
| WO | 2014145564 A3 | 12/2014 |
| WO | 2016109870 A1 | 7/2016 |

* cited by examiner

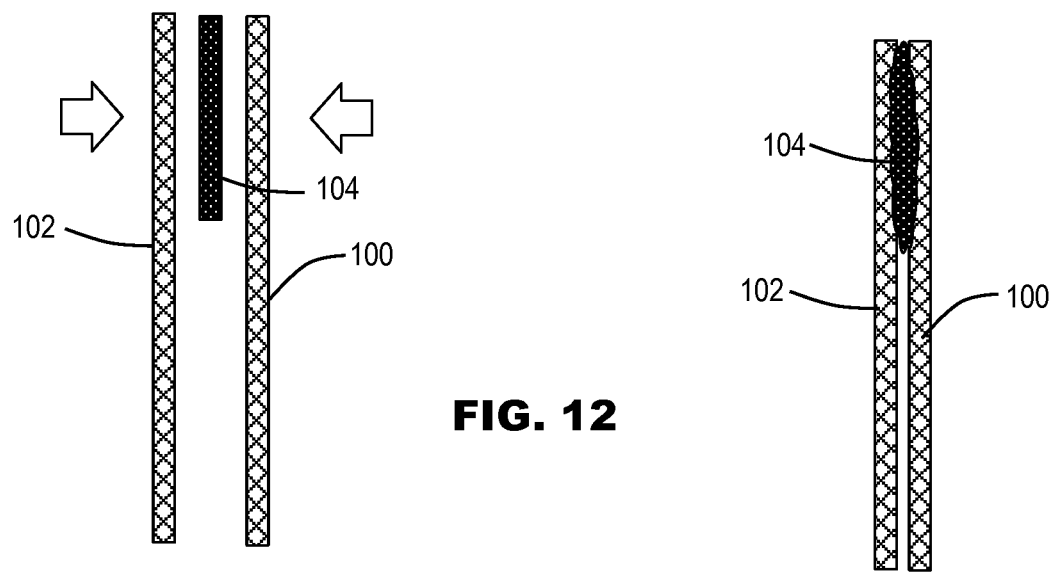
FIG. 12
FIG. 13
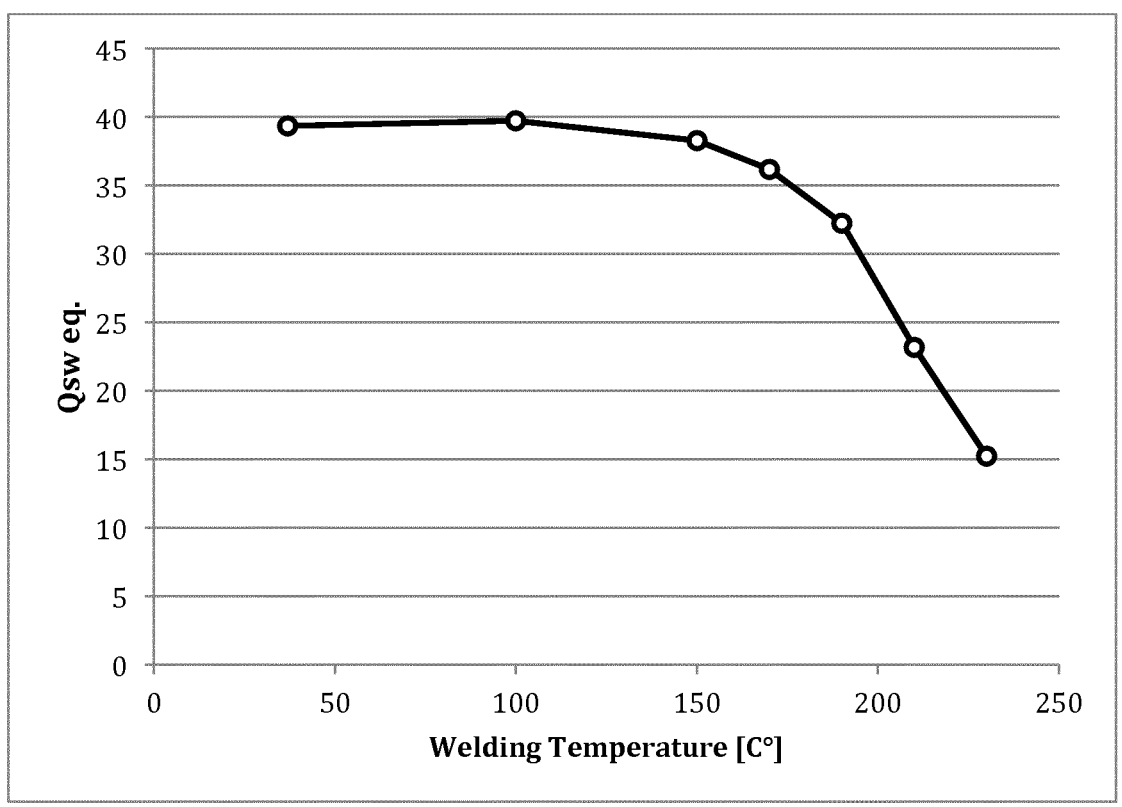

STENT SEALS AND METHOD OF PRODUCTION

CROSS REFERENCE TO RELATED APPLICATIONS

This application is a National Stage of International Application No. PCT/EP2016/052210, filed Feb. 2, 2016, which claims the benefit of European Patent Application No. 15153525.9, filed Feb. 2, 2015, and European Patent Application No. 15164752.6, Filed Apr. 22, 2015, and European Patent Application No 15176367.9, filed Jul. 10, 2015, and European Patent Application No. 15187060.7, filed Sep. 28, 2015, the entire disclosures of which are incorporated herein by reference.

FIELD OF THE DISCLOSURE

The present disclosure relates to the field of stents implantable in the body. Embodiments have been devised to address problems encountered in the field of stent-valves, for example, cardiac stent-valves (e.g. prosthetic heart valves). However, the concepts disclosed herein may have broader application to any stent or prosthesis where as seal is desired at an exterior surface of a stent.

BACKGROUND OF THE DISCLOSURE

WO-A-2013/033791 and US-A-2013/331929 describe expandable sealing means for endoluminal devices, with controlled activation. The devices are said to have the benefits of a low profile mechanism for both self-expanding and balloon-expanding prostheses; contained rather than open release of the material; active conformation to the leak sites such that leakage areas are filled without disrupting the physical and functional integrity of the prosthesis; and on-demand, controlled activation, that may not be pressure activated. Some of the examples illustrate a peel-off removable cover over a mesh.

Further reference may be made to the advancements in WO 2014/072439.

Nevertheless, it remains challenging to implement a seal in a prosthesis, especially a cardiac stent-valve, and whether or not a swellable seal is used. There are many issues including but not limited to manufacturability; reliable attainment of a certain shelf-life in a toxic storage solution; crimpability of the prosthesis for catheterization; hydrogel containment during and after implantation (if a hydrogel is used); ease of preparation and use for a physician; reliable deployment of the seal during and after implantation; reducing risk of seal malfunction; and/or implementing a seal without compromising prosthesis recaptuability/resheathability.

SUMMARY OF THE DISCLOSURE

The following presents a simplified summary of the disclosure in order to provide a basic, non-limiting, understanding of some aspects of the disclosure.

One aspect of the disclosure provides a prosthesis comprising a stent and a seal for obstructing para-prosthesis leakage. The prosthesis is optionally a stent-valve (for example, a cardiac stent-valve, such as an aortic stent-valve). The seal may comprise one or any combination of two or more of the following features, which are all optional:

(a) The seal may comprise swellable material that swells in response to contact with blood (or a blood component);

(b) The seal may comprise a hollow seal envelope (also referred to herein as a cuff or seal chamber) that extends in a generally circumferential direction with respect to the stent. Optionally, the hollow seal envelope may have a toroid configuration, with various different cross-section shapes of the toroid being possible. A toroid configuration can allow migration of the hydrogel to distend the seal where appropriate, and/or enable seal distention around substantially the entire 360° circumference of the stent. Additionally or alternatively, the envelope is, optionally, of material that is flexible and/or compliant in order to be able to follow the irregular contour of a calcified native anatomy.

(c) The swellable material may be substantially captive within an interior of the seal envelope (which may also be referred to as an interior compartment of the envelope).

(d) The envelope may comprise at least one section of material that extends around the entire circumference of the stent, and is continuous in the circumferential direction of the stent. As used herein, the term "continuous" is intended to mean that the material is absent any seam or join-line that interrupts the integrity of the material in the circumferential direction around the stent.

Instead, the section of material is, for example, integrally formed in a closed-loop or ring shape. In some embodiments, the envelope may comprise plural wall portions made of one or more of such sections of material. In some embodiments, the envelope may be substantially entirely composed of one or more sections of such sections of material.

(e) The seal (and/or envelope) may further comprise plural diffusion barrier wall portions that (at least collectively and while intact) substantially enclose the interior compartment to define a diffusion barrier for preventing liquid external to the seal from penetrating into the seal.

(f) Alternatively, the seal (and/or envelope) may comprise a single diffusion barrier wall portion that (at least while intact) substantially encloses the interior compartment for preventing liquid external to the seal from penetrating into the compartment. (Alternatively, in some embodiments, no diffusion barrier wall portion might be provided.)

(g) A diffusion barrier wall portion, if provided, may comprise one or more metallics. As used herein, the term "metallics" is intended to cover any material including metal and/or a metal compound (e.g. an oxide) and/or alloy. Examples of metallics diffusion barrier material include aluminium oxide and/or titanium.

(h) Additionally or alternatively, a diffusion barrier wall portion, if provided, may, for example, comprise a laminate including at least one plastics film layer, and at least one diffusion barrier layer supported by the plastics film layer. Various different diffusion barrier layer materials are envisaged, including by way of example only: metallics (e.g. see above); non-metallics (e.g. all materials other than metallics); glass; polyvinyledine chloride (PVDC); liquid crystal; silicon oxide ($SiO_x$). Optionally plural diffusion barrier layers may be provided, optionally one directly on another, or separated by a plastics film layer. Where plural diffusion barrier layers are used, at least some of the layers may be of the same barrier material and/or at least some of the layers may be of different barrier material. For example, plural diffusion barrier layers may include one or more non-metallics layers (e.g. silicon oxide), and one or more metallics layers (e.g. titanium). In some embodiments, at least two non-metallics layers (e.g. silicon oxide) may sandwich a metallics layer (e.g. titanium). Additionally or alternatively, in some embodiments, a stack of alternating metallics (e.g. titanium) and non-metallics (e.g. silicon oxide) layers may be provided. Additionally or alternatively, in some embodiments, at least two layers of a first barrier material (whether metallics or not) may sandwich a layer of a second barrier material (whether metallics or not). Additionally or alternatively, in some embodiments, a stack of layers of alternating first barrier material (whether metallics or not) and second barrier material (whether metallics or not) may be provided.

(i) In some embodiments, the diffusion barrier layer or material (e.g. each layer and/or combination of layers in some embodiments) may be not substantially greater than about 10 µm thick, optionally not substantially greater than about 5 µm thick, optionally not substantially greater than about 4 µm thick, optionally not substantially greater than about 3 µm thick, optionally not substantially greater than about 2 µm thick, optionally not substantially greater than about 1 µm thick, optionally not substantially greater than about 500 nm thick, optionally not substantially greater than about 300 nm thick, optionally not substantially greater than about 200 nm thick, optionally not substantially greater than about 100 nm thick, optionally not substantially greater than about 50 nm thick, optionally not substantially greater than about 20 nm thick, optionally not substantially greater than about 10 nm thick. Such a thickness (or thicknesses as appropriate) may, for example, be formed by a vapour deposition process, for example, plasma vapour deposition.

(j) At least one diffusion barrier wall portion may be a non-removable integral part of the seal, e.g. of the seal envelope. Such a non-removable wall portion may remain intact with the seal and the prosthesis during and/or after implantation.

(k) Additionally or alternatively to (j), at least one diffusion barrier wall portion may be provided in the form of (or comprised in) a removable cover. Prior to removal, the diffusion barrier wall portion may contribute to preventing diffusion of liquids into the envelope, for example, while the device is stored in a storage liquid environment prior to use. In use, the removable cover is configured to be removed prior to, or during, implantation. Removal of the cover may allow subsequent liquid ingress into the envelope for communication with the swellable material.

(l) At least one diffusion barrier wall portion may be substantially transparent, so as not to obscure substantially the visibility of underlying structure. For example, a removable cover may be substantially transparent.

(m) One or more of the non-removable barrier wall portions may be backed by fabric. The backing may, for example, overlap substantially an entire face of the (or a) non-removable barrier wall portion. The fabric may be joined to the (or a) non-removable barrier wall portion over substantially its entire surface (forming, for example, an integral laminate), or the fabric may be joined to the (or a) non-removable barrier wall portion in one or more discrete regions, for example, around a periphery of the (or a) barrier wall portion. Use of a fabric backing may, for example, provide for easier suturing, and/or provide physical protection and/or reinforcement of the barrier wall portion. The fabric backing may, in some embodiments, extend beyond at least one periphery and/or extremity and/or edge of the (or a) diffusion barrier wall portion.

(n) Whether or not a diffusion barrier wall portion is provided, the envelope may comprise first and second fabric wall portions sandwiching an edge region of a film, and welded together to define a joint between the fabric wall portions and the film. The film may be joined directly to at least one, optionally both, of the fabric wall portions. Additionally or alternatively, the fabric wall portions may optionally extend beyond a periphery of the film, to define a direct fabric-fabric welded region corralling the film edge. Such joint(s) may provide reliable fastening of a film even if one surface of the film is not easily weldable (for example, if the film is a laminate including a surface layer of material, for example, metallics, that is not easily weldable to the fabric).

(o) The envelope may comprise at least one wall portion of at least partly conical shape. The at least one wall portion may, for example, be a radially inner wall portion. The at least partly conical shape may optionally match (or at least generally match) a portion of an outer profile of the stent. The outer profile of the stent may include an at least partly conical stent section.

(p) The envelope may comprise at least a first wall portion of at least partly conical shape, and a second wall portion having an at least partly bulged and/or outward channel shape, the first and second wall portions being joined together at respective axially spaced apart regions at which the diameters of the first and second wall portions substantially match one another.

(q) The envelope may comprise at least one wall portion having an at least partly conical shape, and a second wall portion having an axially collapsed conical shape, the first and second wall portions being joined together at respective axially spaced apart regions at which the diameters of the first and second wall portions substantially match one another. The term "axially collapsed conical shape" as used herein refers to a wall portion that is collapsed axially from an uncollapsed state in which uncollapsed state the wall portion has (and/or would have, and/or had) an at least partly conical shape of axial height greater than in the collapsed state. The second wall portion may not have a truly conical shape in the collapsed state, but axially collapsing a conical shape may nevertheless preserve the respective matching diameters for attaching the first and second wall portions together, while forming an excess of material that is able to distend somewhat to allow seal expansion.

(r) The envelope may comprise one or more wall portions of fabric, and wherein at least when in a state ready for implantation, a radially inwardly facing wall portion abutting against the stent comprises a fabric surface for contacting (or in contact with) the stent, and wherein a radially outwardly facing wall portion comprises a fabric surface for contacting surrounding anatomical tissue upon implantation.

(s) The envelope may comprise fabric substantially entirely enclosing the interior compartment containing the swellable material. Optionally, a region of the fabric may be lined with a substantially non-stretching film (or a laminate including such film). The film may provide local reinforcement of the fabric against stretching. Such a configuration may, for example, be implemented at a region of the cuff facing the stent. The film may reduce any tendency of the fabric to expand through interstices of the stent structure. The configuration may promote swelling of the cuff in a direction away from the stent, and reduce swelling through stent interstices. Optionally, the film may be of, or comprise, plastics.

(t) The envelope may comprise fabric substantially entirely enclosing the interior compartment containing the swellable material. Optionally, a region of the fabric may be lined with a diffusion barrier wall portion to obstruct ingress of liquid through the region of the fabric lined with the diffusion barrier wall portion. The diffusion barrier wall portion may be welded to the fabric, for example, around a periphery of the diffusion barrier wall portion. The diffusion barrier wall portion may be a non-removable integral part of the seal. The diffusion barrier wall portion may have any of the characteristics or constructions previously described.

(u) The seal and/or envelope may comprise a fabric section that has a self-supporting bulged shape. For example, the bulged shape may comprise an annular bulge or annular channel. Additionally or alternatively, the bulged shape may define a region having an outer diameter (relative to a central axis, e.g. of the stent) that is greater than that of first and second regions axially delimiting the bulged shape. Additionally or alternatively, the bulged shape may be radially collapsible and/or may be compliant. This aspect is not limited in any way to seals using swellable material, but may be used with any type of seal, for example, a seal in which a bulged shape may contribute to seal functionality.

(v) The bulged shape may be set in the fabric as a thermoset or thermoformed shape. The shape may include an annular bulge and/or channel configuration.

(w) The envelope may comprise wall portions that are attached together by laser welding.

(x) The envelope, or some other member of a prosthesis, may comprise first and second fabric wall portions joined together at a welded joint, the welded joint comprising a polymeric material having a melting temperature that is lower than that of at least one, optionally both, of the fabric wall portions. Optionally, fibres of the fabric may remain unmelted at the weld, the weld being effected by fusion of the polymeric material to the fibres of the fabric wall portions. In a related aspect, a method of joining first and second fabric wall portions together may generally comprise: arranging a fusible polymeric material at least at a target site for the join between the fabric wall portions (optionally between the fabric wall portions), the fusible polymeric material having a melting temperature lower than that of at least one, optionally both, of the fabric wall portions; subjecting the target site for the join to heat, to fuse the polymeric material to the fabric wall portions to effect a joint at the interface between the fabric wall portions. Optionally, the operation is carried out at a temperature lower than the melting temperature of at least one, optionally both, of the fabric wall portions.

(y) During a manufacturing process involving welding near or around a swellable material (for example, a hydrogel), the hydrogel may be protected from exposure to an elevated temperature that would otherwise significantly degrade the swelling characteristics of the swellable material.

(z) The seal may be constructed in tubular form, and be fitted to the stent in tubular form.

(za) The seal may be incorporated into a skirt of the stent-valve, and be sutured to the stent at positions on both axial sides (e.g. both axially above and below) of the seal. The skirt may comprise fabric. The sutures may be made at positions or regions of the skirt comprising (i) only fabric, or (ii) fabric reinforced by a polymeric material fused to, coated on, impregnated into, or integral with the fabric.

(zb) The seal and/or envelope and/or skirt (e.g. inner and/or outer) and/or some other member of a prosthesis, may comprise a fabric, pores of the fabric being substantially occluded by a polymeric material. For example, the polymeric material may penetrate or impregnate the network of fibres of the fabric. Additionally or alternatively, the at least some of the polymeric material may be provided intra-fibre. The polymeric material may, for example, be a coating on the fabric or a film fused with the fabric. In some embodiments, the fabric may be dip coated with the polymeric material. In some embodiments, the polymeric material may, for example, be or comprise polyurethane. Additionally or alternatively, the fabric may optionally comprise PET.

In a closely related aspect, a method is disclosed comprising coating a fabric with a polymeric material to substantially occlude pores of the fabric with the polymeric material. The method may, for example, comprise dip coating the fabric with the polymeric material, or fusing or melting the polymeric material to the fabric, without substantially melting the fabric.

Use of such polymeric material may reinforce the fabric, and avoid risk of the pores enlarging uncontrollably if the fabric is subjected to stress that might otherwise cause the fabric to stretch and the pores to enlarge. Such stress might, for example, arise during a recapture or resheathing operation to at least partly re-collapse a prosthetic stent valve if the prosthesis is not positioned optimally and/or does not function as desired.

(zc) The seal and/or envelope and/or skirt (e.g. inner and/or outer) and/or some other member of a prosthesis, may comprise a composite material comprising a fabric and a polymeric material carried on, and/or coated on, and/or or impregnated in, at least a first region of the fabric. In the first region, the composite material may combine some characteristics of a fabric, with some characteristics of a polymeric material. For example, like a fabric, the composite material may be suturable to other components, by passing suture thread through positions corresponding to pores of the fabric. The fibres of the fabric may provide a structural network or framework providing resistance to crack propagation from suture holes. Additionally or alternatively, like a polymeric material (e.g. film), the composite may bear stress without substantial pore enlargement. The polymeric material may reinforce the fabric material against pore enlargement; the fabric may reinforce the polymeric material against crack propagation. The composite material may be substantially flexible and/or thermo-formable. The composite material may be weldable and/or fusable and/or heat-sealable to other fabric or composite material.

(zd) The seal and/or envelope and/or skirt (e.g. inner and/or outer) and/or some other member of a prosthesis, may comprise a fabric piece, carrying in one region polymeric material for forming or actually forming a welded joint to another piece or surface (e.g. as aforesaid), and (ii) in another region polymeric material that occludes pores of the fabric and/or reinforces the fabric (e.g. as aforesaid). The polymer material may be the same in both regions, e.g. polyurethane. Optionally a further region of the fabric may have substantially open pores and/or substantially non-occluded pores, e.g. absent the polymeric material.

(ze) The seal and/or envelope may be arranged at an extremity of the stent and/or prosthesis in a region adjacent to one of more attachment elements for releasably attaching the stent to a stent holder of a delivery catheter for the prosthesis.

(zf) The seal and/or envelope may be arranged at an extremity of the stent and/or prosthesis, such that, in use, the seal and/or envelope remains substantially constrained against expansion by a constraining sheath of a deployment catheter until the majority of the stent and/or prosthesis is unsheathed. Such an arrangement can facilitate re-sheathing should this be desirable by an operator.

Additionally or alternatively, a further aspect of the present disclosure may provide a prosthesis, for example a prosthetic cardiac valve, or a seal for a prosthesis, wherein the prosthesis and/or seal comprises a fabric wall portion and a polymeric material fused to the fabric wall portion.

Optionally, any one or more of the following features may also be provided, in any combination, all of the following being optional:

(a) The polymeric material may have a melting temperature that is lower than that of the fabric wall portion.

(b) Fibres of the fabric may remain unmelted at the interface with the polymeric material, the polymeric material being attached to material to the fibres of the fabric wall portion by fusion.

(c) A second fabric wall portion may also be provided, to which the polymeric material is fused.

(d) The polymeric material may provide a welded joint between the fabric wall portions.

(e) The polymeric material may substantially occlude pores of the fabric wall portion.

(f) The polymeric material may or may not extend substantially through the fabric wall portion.

(g) The fabric wall portion may comprise one or more first regions provided with polymeric material fused to the fabric wall portion, and one of more second regions absent said polymeric material.

(h) At least one welded region may be provided in which polymeric material is fused to first and second fabric wall portions to provide a joint between the wall portions, and/or at least one non-welded region may be provided in which polymeric material is fused to only a single fabric wall portion.

(i) The fabric may be a woven fabric.

(j) Fibres of the fabric may be capable of at least partial re-orientation in a region away from the polymeric material, to permit the fabric to adapt to changes in size.

(k) The fabric wall portion and/or the polymeric material may comprises material selected from the group consisting of: polyester; polyethylene terephthalate (PET); polyether ether keeton (PEEK); polypropylene (PP); polytetrafluroth-ylene (PTFE); polyurethane (PU); ultra-high molecular weight polyethylene (UHMWPE); silicone; polyacetal; polyphenylsulfone; polysulfone; polyvinylidene fluoride; polyamide.

(l) The fabric wall portion may comprises polyester (e.g. PET), and/or the polymeric material may comprises polyurethane.

(m) The or a prosthetic cardiac valve may comprise a stent component and a skirt carried by the stent component, wherein the skirt comprises the fabric wall portion.

(n) The skirt may not and/or does not have a peelable cover.

(o) The skirt may define an envelope containing a material that swells when contact by blood or a blood component.

(p) A suture may be provided securing the skirt to the stent component, wherein the suture passes through the polymeric material.

(q) The suture may pass through the fabric wall portion and the polymeric material fused to the fabric wall portion.

(r) The or a prosthetic valve comprising the fabric wall portion may be compressible to a collapsed configuration for introduction to the heart by a catheterization technique, and expandable to an implanted configuration.

A further aspect of the present disclosure may provide a seal or a skirt for a prosthetic cardiac valve, comprising a fabric wall portion and a polymeric material fused to the fabric wall portion. The polymeric material may have a melting temperature that is lower than that of the fabric wall portion. The fibres of the fabric may remain unmelted at the interface with the polymeric material, the polymeric material being attached to material to the fibres of the fabric wall portion by fusion. The polymeric material may provide a welded joint to another fabric wall portion and/or may reinforce the fabric and/or may occlude pores of the fabric.

As used anywhere herein, the term fabric is intended to refer to any woven or non-woven material constructed of a network of fibres or filaments. The terms fibres and filaments are used interchangeably herein. In particular, the fabric may be a woven material.

Although certain features, aspects and ideas have been highlighted above and/or in the appended claims, protection is claimed for any novel feature or idea described herein and/or illustrated in the drawings whether or not emphasis has been placed thereon.

BRIEF DESCRIPTION OF THE DRAWINGS

Non-limiting embodiments of the disclosure are now described, by way of example only, with reference to the accompanying drawings, in which:

In FIG. 2 and subsequent Figs, the seal is shown to the right in section (instead of to the left in FIG. 1, but without any technical consequence).

FIG. 12 is a schematic diagram illustrating a welding technique for joining fabric pieces.

FIG. 13 is a schematic diagram illustrating how the swelling ability of a hydrogel may be affect by exposure to elevated temperatures.

DESCRIPTION OF PREFERRED EMBODIMENTS

Figure 1:
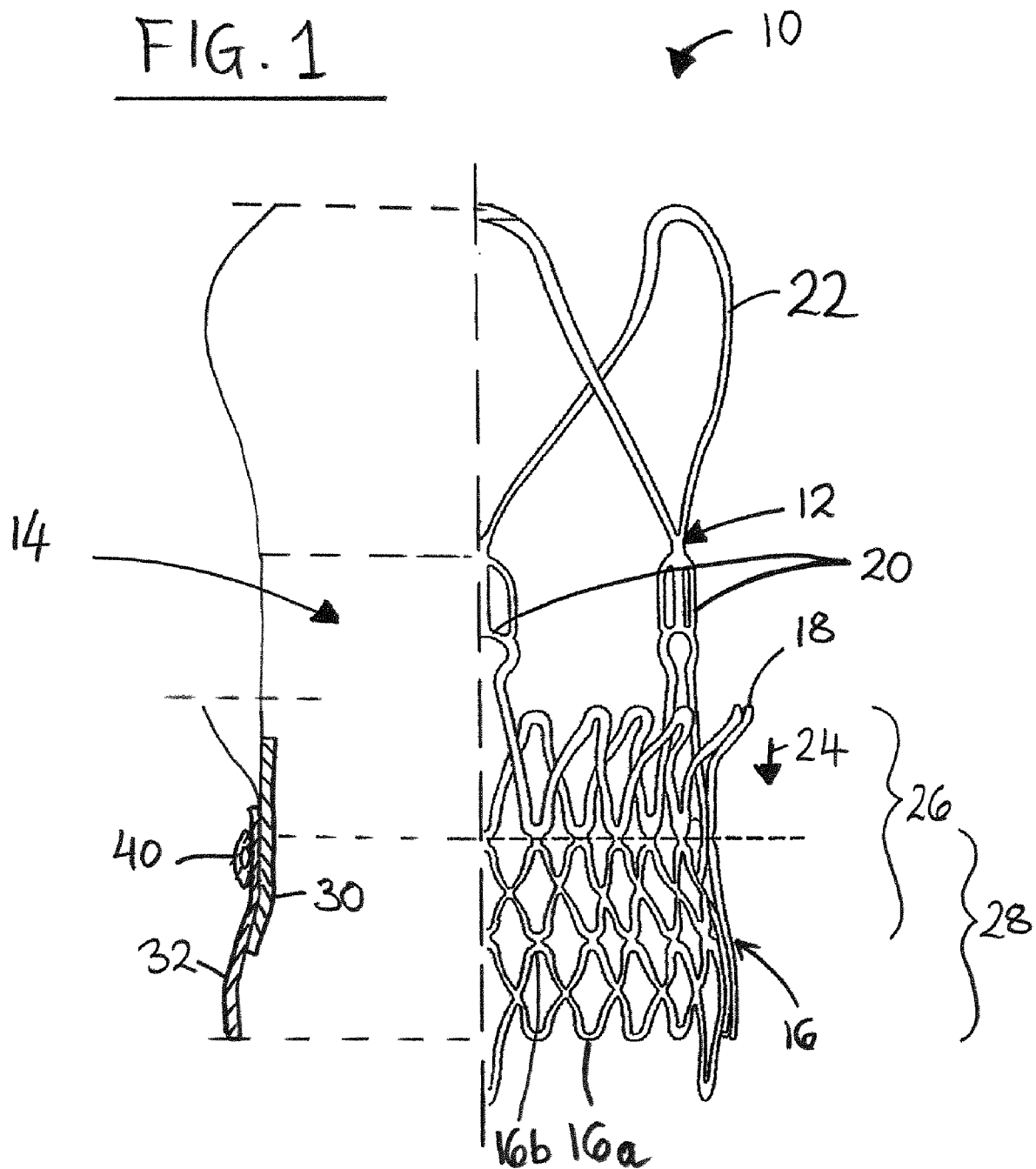
FIG. 1 is a schematic drawing illustrating a stent-valve with which some embodiments of the present disclosure are suitable to be used. The figure is broken along a centre-line of the stent-valve. The stent structure is shown to the right, and a profile showing the positions of the valve, skirt and seal is shown to the left.

Referring to FIG. 1, a stented prosthesis according to some embodiments is illustrated in the form of a stent-valve 10. The stent-valve may include a seal 40 (described further below) for sealing against surrounding tissue when the stent-valve 10 is implanted. The stent-valve 10 may be a cardiac stent-valve, for example, an aortic stent-valve, a mitral stent-valve, a pulmonary stent-valve or a tricuspid stent-valve, for implantation at the respective position in a human heart.

Details of an optional example of stent-valve construction are firstly described, following which details of example seal construction are described in detail.

The stent-valve 10 may be compressible to a radially compressed condition (not shown) for delivery using a delivery catheter (not shown), and be expandable to an operative or expanded condition (similar to that shown) at implantation. The stent-valve 10 may comprise a stent 12 carrying a plurality of leaflets defining a valve 14 (the position of which is depicted schematically by the bounding phantom lines). Various geometries of stent 12 may be used. In some embodiments, the stent 10 may include one or more of: a lower tubular or crown portion 16 (e.g. defining an inlet section), an upper crown portion, a plurality of upstanding commissural supports 20, and a plurality of stabilization arches 22. The stent 12 may have opposite first and second extremities. The lower tubular crown portion 16 may define a first extremity of the stent. The upper crown portion 16 may have a free edge that is positioned between (e.g. and spaced from) both extremities. The commissural supports 20 may optionally be spaced from both extremities. The stabilization arches 22 may extend between the commissural supports 22 and the second stent extremity. The stabilization arches 22 may define the second stent extremity (e.g. the tips and/or arch-apexes of the stabilization arches 22 may define the second stent extremity). The stabilization arches 22 may arch over, and interconnect, the commissural supports 20. Additionally or alternatively to any of the above, the stabilization arches 22 may be bendable or capable of flexing, relative to the commissural supports 20, substantially independently of one another.

In use, the lower portion of the stent 12 may be configured to be deployed after the other regions of the stent 12. For example, the arches 22, the supports 20 and the upper crown 18 may be deployed at least partly before the lower portion 16 (in that order, or in reverse order, or in a different order). At least once the upper crown 18 has been at least partly deployed, the stent 12 may be urged and/or displaced in the direction of arrow 24 to seat the upper crown 18 against native leaflets at the implantation site. Deploying the lower portion 16 last fixes the stent 12 in its final position.

The lower portion 16, and optionally a portion of the upper crown 18, may be formed by a lattice structure of the stent. The lattice structure may define cells or apertures or interstices, for example, generally diamond-shaped apertures (although in some embodiments not strictly diamond-shaped).

The native leaflets may generally overlap a portion 26 of the stent. The native valve annulus may overlap a portion 28 of the stent.

Optionally, the stent-valve 10 may further include an inner skirt 30 communicating with the leaflets 14 and carried on an interior of the stent 12. Optionally the inner skirt 30 is coupled directly to the leaflets 14. Additionally or alternatively, the stent-valve 10 may further comprise an outer skirt 32 carried on an exterior of the stent 12. When both skirts are provided, the skirts may at least partially overlap. In some embodiments, one skirt (e.g. the outer skirt 32) may optionally extend further towards a lower extremity of the stent 12 than the other (e.g. inner skirt 30). Additionally or alternatively, one skirt (e.g. the inner skirt 30) may optionally extend further towards an upper extremity of the stent 12 than the other (e.g. outer skirt 32). The skirts may be of any suitable flexible and/or compliant material, for example, fabric (e.g. of PET) or of biological tissue (e.g. of pericardium). The skirts may be of the same specific material, or of the same type of material (e.g. biological tissue, fabric), or of different types of material. In some examples described below, the outer skirt 32 may of fabric; the inner skirt may be of fabric or of biological material as desired.

Optionally, the inner and outer skirts 30 and 32 may be secured directly to each other along at least one substantially continuous or discontinuous line of attachment. The attachment may, for example, be by one or more of: suturing, welding, fusion, adhesive. The line of attachment may optionally extend around the entire circumference of the stent-valve. The attachment may mitigate risk of leakage of blood in the spaces of the stent between the inner and outer skirts 30 and 32.

Optionally, at least the outer skirt 32 is positioned to leave the upper crown 18 substantially unobscured by the outer skirt 32. Such an arrangement may assist good blood flow to the coronary arteries (for example, in the case of a stent-valve for the aortic valve).

In some embodiments, the lower portion 16 has an extremity (e.g. lower or inlet extremity) formed with a substantially zig-zag shape. The zig-zag shape may comprise lower apexes 16a and upper apexes 16b. The upper apexes 16b may be masked in FIG. 1 by the superimposed presentation of both the frontmost and rearmost cells of the lattice structure. The zig-zag shape may be substantially continuous around the circumference of the stent 12—The outer skirt 32 may have a peripheral edge having a zig-zag shape that matches substantially the zig-zag shape of the extremity of the lower portion 16. Such an arrangement can avoid excessive material at the extremity, and thereby facilitate crimping of the stent-valve 10. At the same time, outer skirt 32 covers (for example, complete) open cells of the lattice structure down to the stent extremity to reduce risk of blood leakage through the apertures of the cells. The outer skirt 32 can also provide a layer of material over the struts of the stent, thereby to cushion the engagement between the stent and the sensitive native heart tissue.

The stent-valve 10 (e.g. the valve 14) may optionally comprise biological tissue (for example, pericardium (such a porcine pericardium and/or bovine pericardium) and/or natural cardiac valve leaflets (for example, natural porcine cardiac valve leaflets, optionally attached to a portion of natural cardiac wall tissue)). The biological tissue may be fixed, for example, using glutaraldehyde.

The stent 12 may optionally be of a self-expanding type that is compressible (e.g. crimped) to a compressed configuration for loading into a delivery catheter (not shown) having a sheath for constraining the stent in the compressed configuration for delivery to the site of implantation. In use, by removal of the constraining effect of the sheath, the stent 12 self-expands to or towards the operative configuration. A self-expanding stent may, for example, be of shape-memory material, for example, shape-memory metal alloy, for example, a nickel-titanium alloy (e.g. nitinol). Additionally or alternatively, the stent 12 may be configured to be expanded by application of an axial foreshortening force from the delivery catheter and/or by application of a radial expanding force from the delivery catheter, such as by using an expansion balloon.

The stent-valve 10 may further comprise the seal 40 for sealing against surrounding native tissue when the stent-valve 10 is implanted. The seal 40 may be arranged at any suitable position on the stent 12. In some embodiments, the seal 40 may be arranged between the extremity of the upper crown portion 18 and the extremity of the lower crown or tubular portion 16. In some embodiments, the seal 40 may be positioned optionally closer to the upper crown portion 18, alternatively optionally closer to the lower crown or tubular portion 16, alternatively optionally midway between the extremities of the two crown portions 16 and 18, alternatively optionally at a waist or trunk section between the two crown portion 16 and 18. In some embodiments, the seal 40 is carried on the exterior of the stent 12.

As mentioned above, in some embodiments, the (e.g. lower or inlet) periphery of the stent 12 has a substantially zig-zag shape. The zig-zag shape may comprise lower apexes 16a and upper apexes 16b. If desired, the seal 40 may be arranged to be positioned only between the extremity of the upper crown 18 and the upper apexes 16. For example, the seal 40 might not extend to occupy space between the upper apexes 16b and the lower apexes 16a. Positioning the seal 40 clear of the lower apexes 16a can reduce the bulk of material at the extremity, and facilitate crimping. Additionally or alternatively, the seal may be positioned so as not to cover substantially the upper crown 18. Leaving the upper crown 18 clear may enhance blood flow to coronary arteries (for example, in the case of a replacement valve for the aortic valve position).

The seal 40 may be configured for sealing against surrounding native tissue when the stent-valve 10 is implanted. In some embodiments, the seal 40 may be provided as an integral part of the stent-valve 10.

Figure 2:
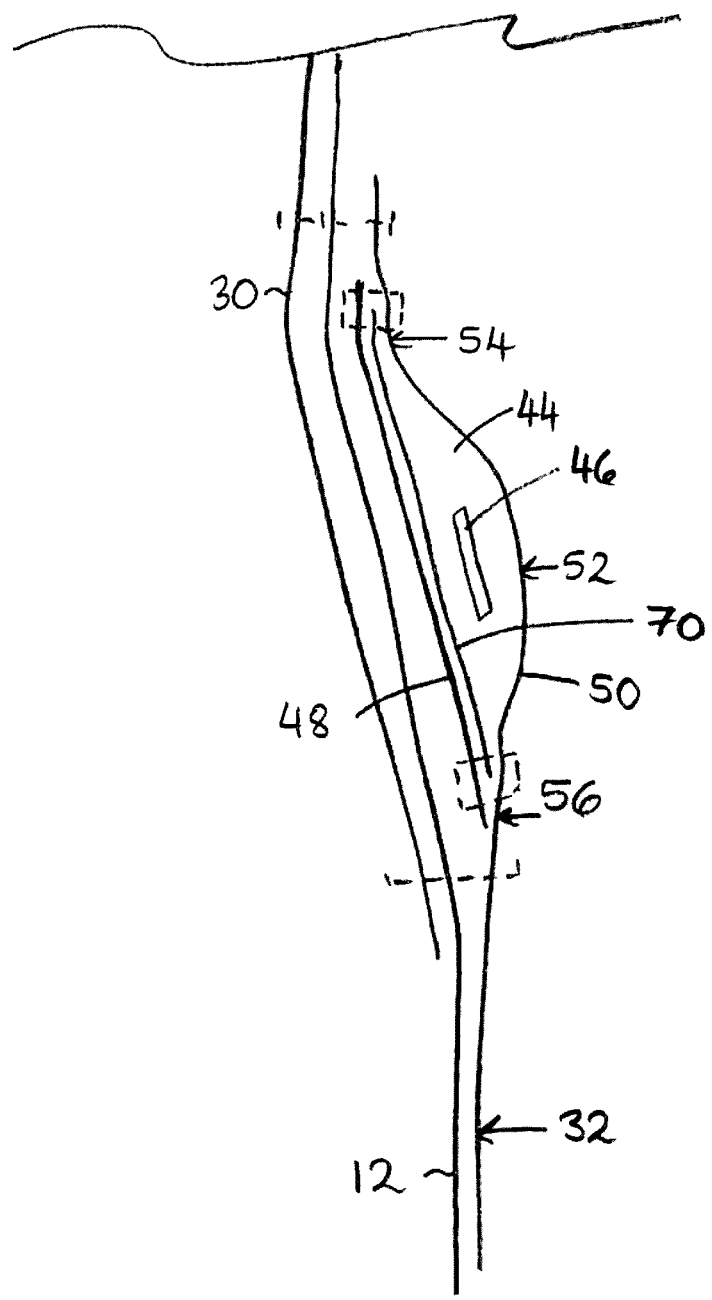
FIG. 2 is an enlarged schematic section showing the seal 40 of FIG. 1 in more detail.

Referring to FIG. 2, the seal 40 is illustrated in a form incorporated within the outer skirt 32, in order to provide a convenient construction and mounting of the seal 40. However, the same principles may be used in other embodiments in which the seal 40 is not so incorporated.

The seal 40 may comprise a hollow envelope 42 arranged to extend circumferentially around the stent 12, and to define an interior compartment 44 containing swellable material 46 that swells in response to contact with blood (or a blood component). In some embodiments, the seal envelope 42 has a toroid configuration to define a circumferentially continuous interior compartment 44. The swellable material 46 may be captive within the envelope 42. Various types of swellable material may be used, including but not limited to hydrogels, and/or superabsorbent materials. Examples of suitable material are referred to in the aforementioned specifications.

In some embodiments, the envelope 42 comprises a first, e.g. radially inner wall portion 48, and a second, e.g. radially outer, wall portion 50. In some embodiments, the first and second wall portions 48 and 50 may be formed of distinct pieces of material joined together. In some other embodiments, the first and second wall portions 48 and 50 may be, or comprise respective portions of, a single piece of material folded to define an envelope shape. Other constructions are also envisaged, and the following description applies to all constructions.

In the illustrated form, the second wall portion 50 may be axially longer than the first wall portion 48. The second wall portion 50 may define generally the exterior surface of the outer skirt 32, thereby avoiding any exposed seams or join lines or other abrupt discontinuities that might complicate the ability (i) to slide the stent-valve axially through a compressing funnel for compressing or "crimping" the stent-valve, and/or (ii) to recapture the stent-valve into a catheter should this be desired during implantation. In some embodiments described later, the skirt 32 may include a generally axially extending seam or join-line. An axially extending seam or join-line also may avoid a circumferentially extending discontinuity, and therefore may avoid complicating the ability to crimp the stent-valve and/or recapture the stent-valve, as mentioned above.

The second wall portion 50 may include the zig-zag skirt edge previously described.

The radially inner wall portion 48 may optionally be generally, or at least partly, conical in shape. The radially inner wall portion 48 may optionally substantially match a, e.g. partly conical, shape of the lower portion of the stent 12. In other embodiments, the inner wall portion 48 may be generally non-conical and/or may not match the shape of the lower portion of the stent 12. For example, one or both of the wall portions 48 and 50 may be generally cylindrical in shape.

The second wall portion 50 may optionally have a bulged or bulgeable region 52, delimited axially on either side (e.g. delimited from above and below) by regions 54 and 56 that substantially match the diameter of respective regions of the first wall portion 48, in order to provide zones of attachment between the first and second wall portions.

In other embodiments, the inner wall portion 48 may be generally non-conical and/or may not match the shape of the lower portion of the stent 12. For example, one or both of the wall portions 48 and 50 may be generally cylindrical in shape.

The first and second wall portions 48 and 50 may be of any suitable material or materials, including biological, natural or synthetic materials. In some embodiments, the first and second wall portions are of, or comprise, fabric. The fabric may be the same or similar in both wall portions, or different fabric may be used for each. The fabric may be provided as one or more pieces joined together to define a torroid and/or annular form.

In one example, the fabric may have a thickness of at least about 10 microns, optionally at least about 20 microns, optionally at least about 30 microns, optionally at least about 40 microns, optionally about 40 microns. Additionally or alternatively, the fabric may have a thickness of not substantially more than about 100 microns, optionally not substantially more than about 75 microns, optionally not substantially more than about 50 microns, optionally not substantially more than about 25 microns.

Additionally or alternatively to any of the above thickness examples, the fabric may have a pore-size of at least about 10 microns, optionally at least about 15 microns, optionally at least about 20 microns, optionally about 20 microns. Additionally or alternatively, the pore-size may be not substantially more than about 50 microns, optionally not substantially more than about 100 microns, optionally not substantially more than about 75 microns, optionally not substantially more than about 50 microns, optionally not substantially more than about 25 microns.

Figure 3:
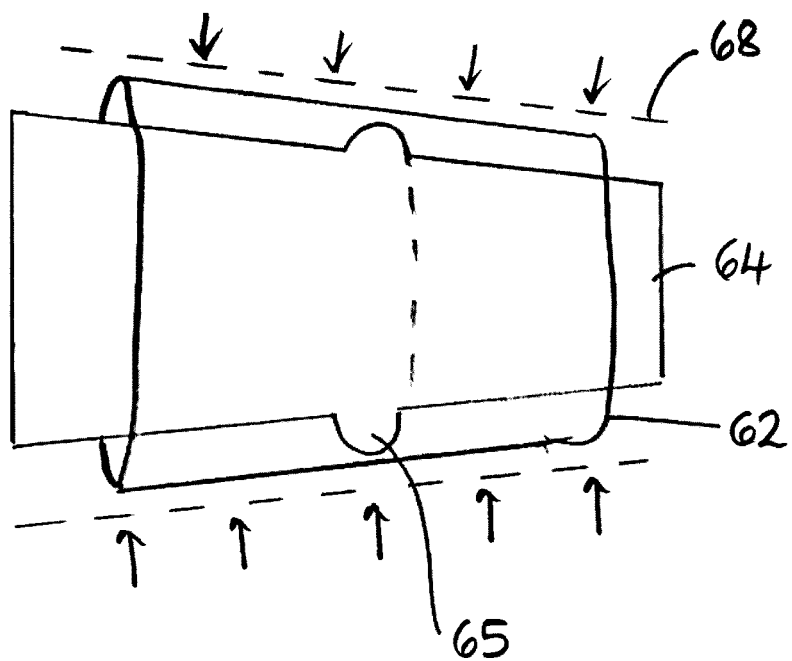
FIG. 3 is a schematic view illustrating a technique for setting a shape in a fabric tube.
Figure 4:
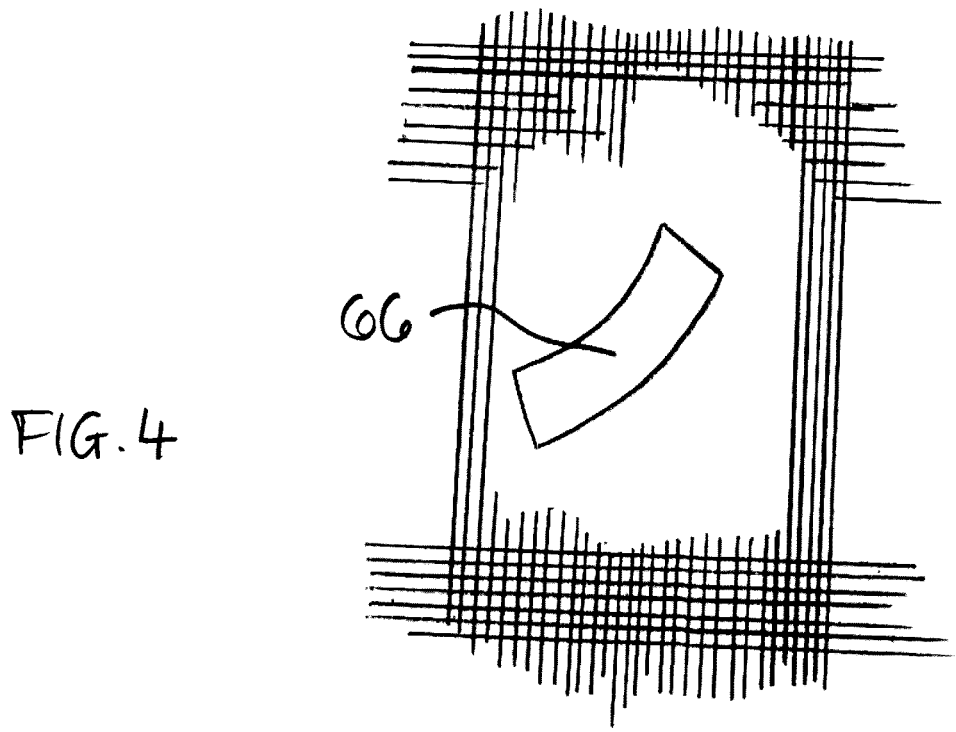
FIG. 4 is a schematic view illustrating cutting of a material blank from fabric sheet, obliquely to the orthogonal weave and/or thread directions of the fabric.

In the form illustrated in FIG. 2, the region 52 of the second wall portion 50 may optionally have a self-supporting bulged shape, although some other embodiments disclosed herein may not use such a self-supporting bulged shape. The region 52 may extend radially outwardly to a respective diameter that is larger than the diameter of the regions 54 and 56 that delimit the region 52. The region 52 may be flexible and/or compliant. Such a form or shape may, for example, be thermoformed or thermoset in the material. For example, referring to FIG. 3, a material 62 (e.g. fabric) may be set by placing a tube of material on a mandrel 64 having an outer profile representative of the shape to be set in the material, and including a corresponding annular bulge 65. The bulge may be of any cross-section or profile shape desired. Merely by way of example, the bulge 65 my have a profile that is any of rounded, arcuate, semi-circular, triangular, or trapezoid. The tube of material 62 may be generally or at least partly cylindrical, and/or it may be at least partly conical. The material 62 may be provided in an integral tubular form, or a tube shape may be formed by wrapping and securing material cut from sheet to define the tube shape. In the case of fabric (whether cut from sheet, or provided in integral tubular form), in some embodiments the direction of the weave and/or fibres may be oblique to the axial direction and/or circumferential directions of the tube. For example, referring to FIG. 4, a blank 66 of fabric material may be cut to form a partly conical shape when wrapped into tubular form, the blank of fabric being cut in a direction oblique to the direction of weave and/or the direction of the fibre of the fabric. Cutting oblique to the direction of weave and/or the direction of the fibre may provide reduced resistance to deformation for thermosetting.

Referring again to FIG. 3, the shape defined by the mandrel may be set into the material 62, for example, by using a heat and shrink technique. In some embodiments, a heat shrink sleeve 68 may be fitted or wrapped around the material 62. Upon suitable heating, by a combination of the heat shrink material 68 tending to shrink against the mandrel 64, and heat deformation of the material 62, the material 62 may be drawn against the surface of the mandrel 64 (as indicated by the arrows). Upon subsequent cooling, the material becomes set or molded in the thus-defined shape. Additionally or alternatively to heat-shrink material, positive and/or negative pressure may be applied in combination with heat, to draw the material against the mandrel to effect the thermosetting/thermoforming.

Whether or not such a shaping operation is used, in the case of fabric (whether cut from sheet, or provided in integral tubular form), in any embodiment described herein, the direction of the weave and/or fibres may be oblique to the axial direction and/or circumferential directions of the tube. Such a direction of weave and/or the direction of the fibre may enhance the functional conformability of the fabric, for example, during crimping of the stent-valve, and/or, during distension of the outer wall portion 52 when the swellable material expands (whether or not set with a self-supporting bulged shape).

Referring again to FIG. 2, at least one of the wall portions (e.g. the first wall portion 48) may optionally comprise (or optionally further comprise) a barrier wall portion 70, for example, effective to obstruct liquid diffusion. If provided, the barrier wall portion 70 may, for example, be or comprise metallics and/or non-metallics. In some embodiments, the barrier wall portion 70 may comprise a laminate including at least one plastics film layer, and at least one diffusion barrier layer supported by the film layer. Various different diffusion barrier layer materials are envisaged, including by way of example only: metallics; non-metallics; glass; polyvinylidine chloride (PVDC); liquid crystal; silicon oxide ($SiO_x$). Optionally plural diffusion barrier layers may be provided, optionally one directly on another, or separated by a plastics film layer. Where plural diffusion barrier layers are used, at least some of the layers may be of the same barrier material and/or at least some of the layers may be of different barrier material. For example, plural diffusion barrier layers may include one or more non-metallics layers (e.g. silicon oxide), and one or more metallics layers (e.g. titanium). In some embodiments, at least two non-metallics layers (e.g. silicon oxide) may sandwich a metallics layer (e.g. titanium). Additionally or alternatively, in some embodiments, a stack of alternating metallics (e.g. titanium) and non-metallics (e.g. silicon oxide) layers may be provided. Additionally or alternatively, in some embodiments, at least two layers of a first barrier material (whether metallics or not) may sandwich a layer of a second barrier material (whether metallics or not). Additionally or alternatively, in some embodiments, a stack of layers of alternating first barrier material (whether metallics or not) and second barrier material (whether metallics or not) may be provided.

In some embodiments, a combination of titanium and silicon oxide layers may be used. The silicon oxide can complement the manner in which the titanium is deposited, for example, when a vapour deposition process is used. The titanium may be deposited in a columnar manner, while the silicon oxide can fill gaps, valleys or trenches in the titanium or other layer or surface, enabling better adhesion and improved barrier properties.

In some embodiments, the diffusion barrier layer or material (e.g. each layer and/or combination of layers in some embodiments) may be not substantially greater than about 10 μm thick, optionally not substantially greater than about 5 μm thick, optionally not substantially greater than about 4 μm thick, optionally not substantially greater than about 3 μm thick, optionally not substantially greater than about 2 μm thick, optionally not substantially greater than about 1 μm thick, optionally not substantially greater than about 500 nm thick, optionally not substantially greater than about 300 nm thick, optionally not substantially greater than about 200 nm thick, optionally not substantially greater than about 100 nm thick, optionally not substantially greater than about 50 nm thick, optionally not substantially greater than about 20 nm thick, optionally not substantially greater than about 10 nm thick. Such a thickness (or thicknesses as appropriate) may, for example, be formed by a vapour deposition process, for example, plasma vapour deposition.

Figure 5:
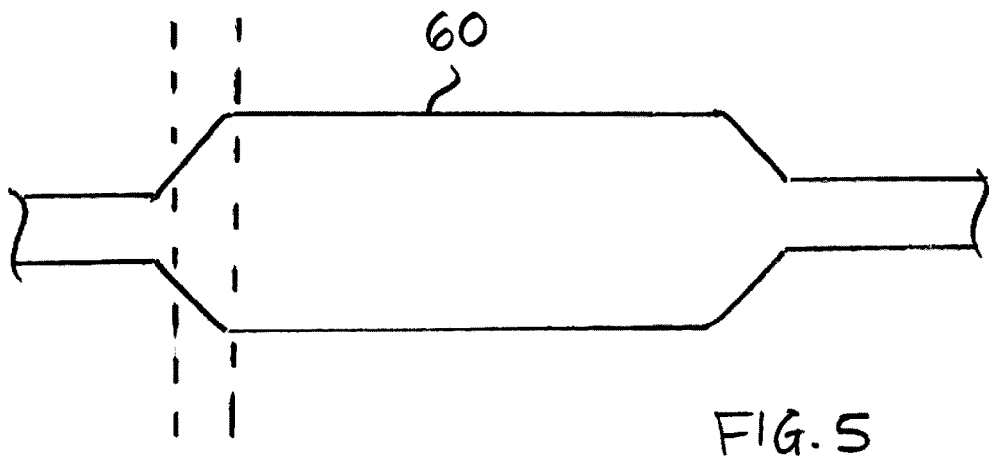
FIG. 5 is a schematic view illustrating cutting of a conical film section from a catheter balloon.

In the illustrated form, the barrier wall portion 70 (if provided) may have an at least partly conical shape, for example, substantially matching the shape of the underlying stent 12, as described above. The barrier wall portion 70 may comprise a film that extends around the circumference of the stent 12, and is continuous in the circumferential direction of the stent. For example, the film may have an integral closed-loop or ring shape. Referring to FIG. 5, such a film may, in some embodiments, be obtained by cutting the film from a catheter balloon 60 (e.g. valvuloplasty balloon). The position from which the film is cut, and the balloon diameter may be selected to obtain the desired shape, slant angle and diameter of the film. A typical valvuloplasty balloon includes two conical portions, which may allow two different portions to be cut from the same balloon.

By using a circumferentially continuous barrier wall portion (e.g. film, and optionally cut from a balloon), a strong and continuous barrier may be implemented reliably, without a complicated structure.

In the illustrated form, the barrier wall portion 70 (if provided) may be a non-removable, integral part of the stent-valve, and/or seal 40, and/or the envelope 42, that remains intact and/or in place when the stent-valve 10 is implanted. For example, the barrier wall portion 70 is implanted with the stent-valve.

Figure 6:
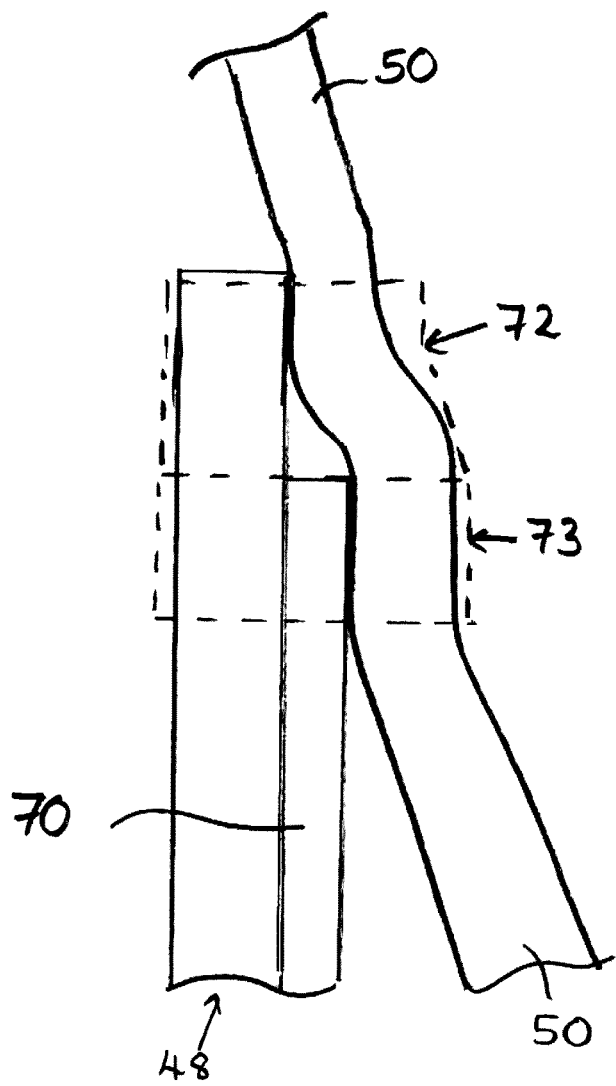
FIG. 6 is a schematic section illustrating a weld detail of FIG. 2.

Referring to FIG. 6, the barrier wall portion 70 (if provided) may be attached to the fabric of the first wall portion 48 and/or to the second wall portion 50 at a combined seam 74 at which the barrier wall portion 70 is sandwiched. The barrier wall portion 70 may be joined directly to at least one, optionally both, of the fabric of the wall portions 48 and 50, for example, by weld 73. Additionally or alternatively, the fabric of wall portions 48 and 50 may optionally extend beyond a periphery of the barrier wall portion, to define a direct fabric-fabric welded region 72 corralling the edge of the barrier wall portion 70. Such joint(s) may provide reliable fastening of a barrier wall portion 70 even if one surface of the barrier wall portion 70 is not easily weldable (for example, if the barrier wall portion is a film laminate including a surface layer of material, for example, metallics, that is not easily weldable directly to the fabric).

In some embodiments, laser welding may be used to effect the welded seam 74 (including the regions 73 and 72). Laser welding may enable a precise, and uniform weld joint to be made with good control.

In some embodiments, the axial dimension of each weld region 72 and 73 may be about 1 mm, such that the combined weld 74 has an axial dimension of about 2 mm. The axial dimension of the envelope 42 (between the regions 54 and 56) may be less than about 10 mm, optionally less than about 9 mm, optionally less than about 8 mm, optionally less than about 7 mm, optionally less than about 6 mm.

In some embodiments, the radial dimension of the bulge 52 relative to first wall portion 48 may be at least 1 mm, optionally at least 2 mm, optionally at least 3 mm.

The first and second wall portions 48 and 50 may optionally have rather different properties from each other in the region of the seal 40. The second wall portion 50 (e.g. of fabric) may be porous to allow passage of blood or a blood component therethrough into the interior compartment 44 for communicating with the swellable material 46. The second wall portion 50 may be flexible and/or compliant to allow the seal 40 to distend to fill gaps between the stent-valve and the native anatomy. In contrast, the barrier wall portion 70 (if provided) of the first wall portion 48 may provide a substantially liquid impermeable barrier preventing any liquid transmission through the first wall portion 48 into the interior compartment 44. Additionally, the e.g. film and/or metallics, construction of the barrier wall portion 70 (if provided) may be substantially inextensible, reinforcing the first wall portion 48 against radially inward deformation when the seal 40 swells. This can obstruct inward swelling of the seal 40 through the interstices of the stent 12, and instead promote outward swelling of the seal 40. At the same time, the use of e.g. fabric in the first and second wall portions 48 and 50 can provide a cushioning effect as part of the envelope, reducing risk of damage to the seal envelope 42 and the swellable material 46 during production and/or storage and/or implantation and/or post-implantation. The fabric can also be directly sutured to the stent 12 and/or to the inner skirt 30. For example, at least one, optionally at least two suture lines may be shown in FIG. 2 by broken lines, respectively axially above and/or below the envelope 42, joining the outer skirt to the stent and/or the inner skirt. Optionally, the use of sutures above and below the envelope 42 can additionally or alternatively provide support for the envelope 42 material that obstructs inward swelling of the seal 40, by anchoring the envelope 42. Further sutures (not shown) may also attach the lower edge of the outer skirt 32 to the stent (e.g. below the lower suture indicated by a broken line).

Figure 7:
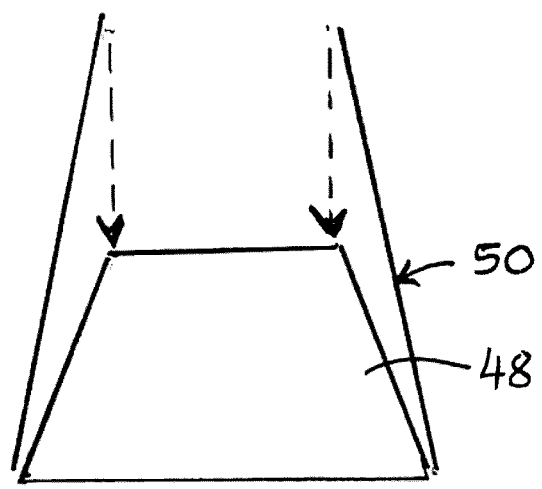
FIG. 7 is a schematic view illustrating a technique for forming an axially collapsed conical skirt portion.
Figure 8:
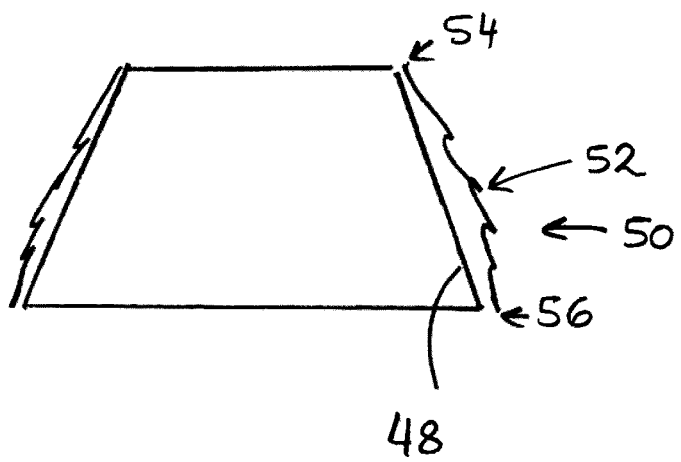
FIG. 8 is a schematic view illustrating the skirt with the outer wall portion after axial collapsing.

Referring to FIGS. 7 and 8, an alternative envelope construction technique is illustrated. The following description focuses on the differences compared to the preceding construction. The alternative construction may include any of the features and/or characteristics described above, whether or not explicitly mentioned.

Referring to FIG. 7, as an alternative to a shape setting technique defining a self-supporting bulge shape, the region 52 may comprise excess material that allows the region 52 to be at least partly bulgeable or distensible. The region 52 may be defined by an axially collapsed conical shape, the first and second wall portions 48 and 50 being joined together at respective axially spaced apart regions 54 and 56 at which the diameters of the first and second wall portions substantially match one another. As best illustrated in FIG. 7, the term "axially collapsed conical shape" describes a wall portion that is initially produced as a conical shape of axial height greater than the intended spacing of the regions 54 and 56, but having diameters to match the regions 54 and 56 when collapsed axially. The portion 52 may not have a truly conical shape in the collapsed state, but axially collapsing a conical shape may nevertheless preserve the respective matching diameters for attaching the first and second wall portions 48 and 50 together, while forming an excess of material that is able to distend somewhat to allow seal expansion.

Figure 9:
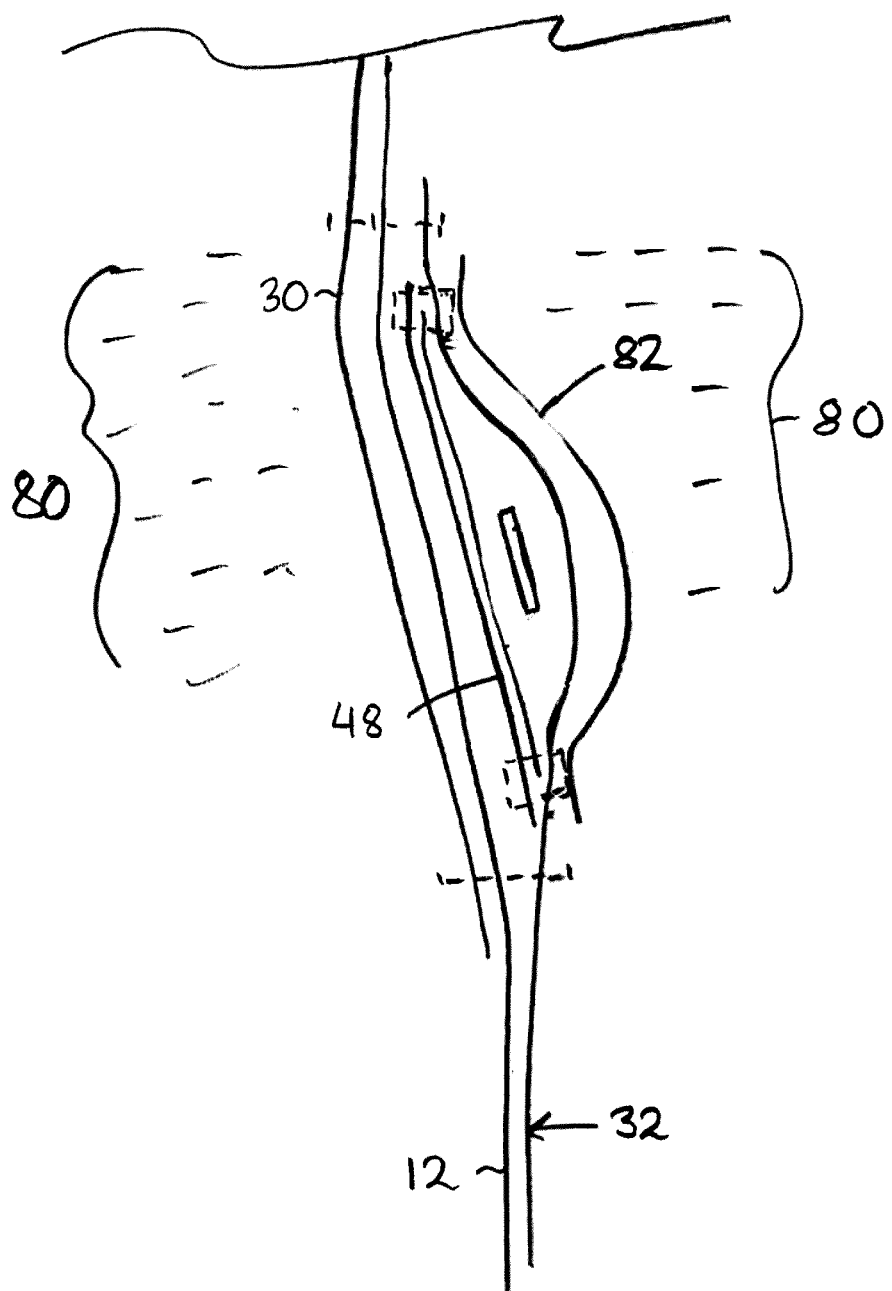
FIG. 9 is a schematic view similar to FIG. 2, illustrating storage of the stent-valve in a liquid storage solution.

Referring to FIG. 9, prior to use for implantation, the stent-valve 10 (of any of the aforementioned constructions) may be stored in a storage liquid 80 to preserve its sterility and/or avoid damage to the leaflets. For example, the storage liquid may be a glutaraldehyde solution and/or an alcohol solution. In order to protect the seal 40 against ingress of storage liquid into the seal 40, the seal 40 may optionally further comprise a removable cover 82 covering the region of the second wall portion 50 at the seal envelope 44. The removable cover 82 may, for example, be of liquid impermeable material and/or comprise a barrier wall portion similar to that described for barrier wall portion 70 (if provided). For example, the cover 82 may comprise metallics or a film carrying one or more layers of barrier material deposited on the film. The removable cover 82 may be welded at positions 84, for example, in register with the welds 72. Collectively, the removable cover 82 and the barrier wall portion 70 may define a liquid impermeable barrier protecting the envelope against liquid ingress, even during prolonged storage times.

In the form illustrated, the cover 82 may have a shape to match the bulge 52. In other embodiments (not shown explicitly), the bulge 52 may be radially collapsible or foldable towards the first wall portion 48, and the cover 82 may lie flatter with respect to the first wall portion 48 if desired.

In use, the removable cover 82 (if provided) may be peeled from the seal envelope 42 during preparation of the stent-valve 10 for implantation, for example after rinsing the stent-valve (once removed from the storage solution to clean the storage solution from the stent-valve). The positions of the welds 84 can avoid any damage to the underlying envelope during peeling. The peeling force is withstood by the relatively strong weld regions 72 and/or 72 and/or 74.

Figure 10:
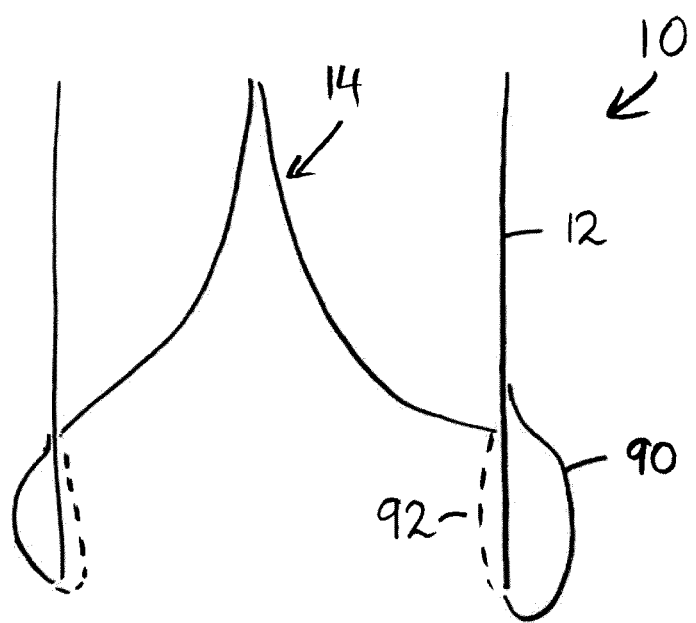
FIG. 10 is a schematic section through a further example of stent-valve including a thermoset fabric skirt.

Referring to FIG. 10, a further embodiment is illustrated in the form of a stent-valve 10 carrying a fabric seal skirt 90 without using a swellable material. The fabric seal skirt 90 may be set (e.g. thermoset or thermoformed) to have a bulged shape, using the techniques described previously with respect to FIG. 3 of the drawings. The fabric skirt may therefore have a self-expanding characteristic to expand gently and/or conformably into contact with surrounding anatomy to fill any gaps between the stent-valve 10 and the surrounding anatomy. The skirt 90 may be arranged substantially outside the stent 12 or, in some embodiments, a portion 92 of the skirt 90 may be folded towards the interior of the stent 12 to define an integral inner skirt (optionally coupled to the leaflets 14). The skirt 90 may comprise a single piece of fabric, or it may comprise plural pieces of fabric attached together along one or more seams. The pieces may be attached by sutures and/or by welds (e.g. laser welds) as described previously and further explained below.

Figure 11:
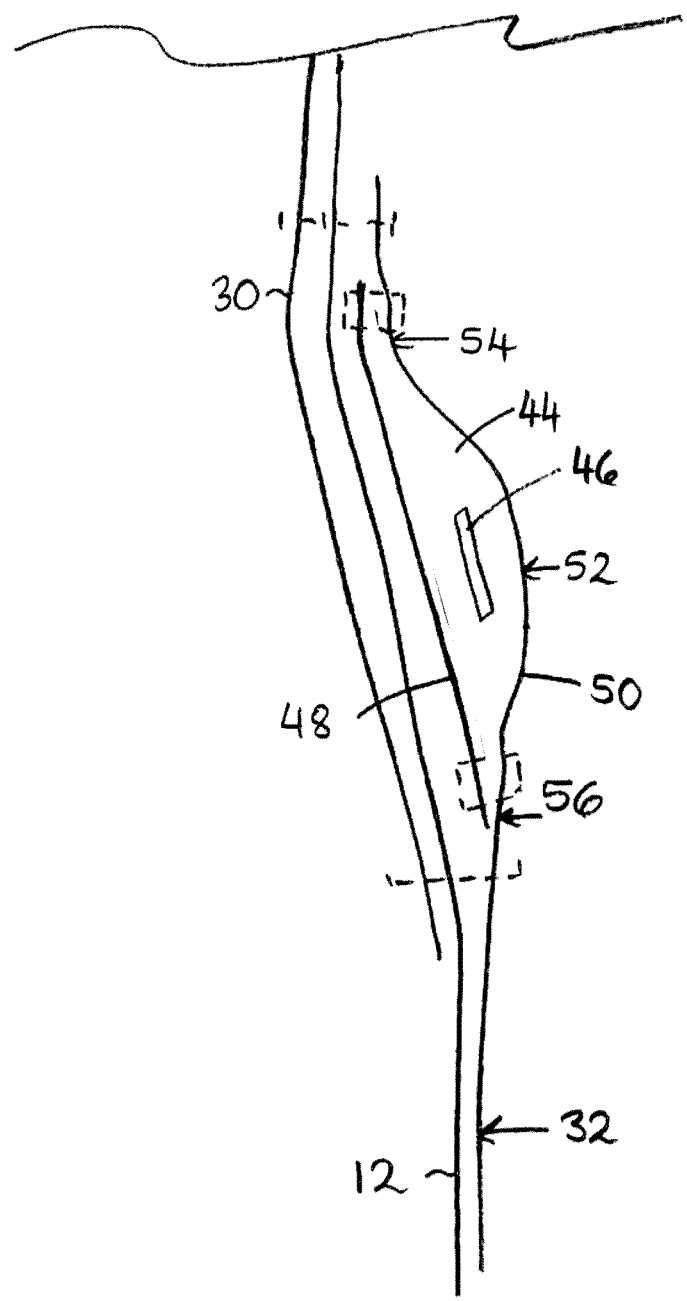
FIG. 11 is a schematic section through a further example of skirt structure similar to that of FIG. 2.

FIG. 12 illustrates a welding technique usable in some embodiments of the present disclosure for joining at least first and second fabric pieces or wall portions 100 and 102. The fabric pieces 100 and 102 may be of the same material, or different materials. The welding technique may, for example, be suitable for the welded joints 54 and 56 of FIGS. 2 and 11. A polymeric fusible material 104 is provided at least in the target region for the join. The polymeric fusible material may, for example, be a film 104 arranged between the fabric pieces 100 and 102, for example, in the target region for the join. Additionally or alternatively, the polymeric fusible material may be carried by one or both of the fabric pieces 100 and 102. For example, a fabric piece 100 and/or 102 may be impregnated with the polymeric fusible material. Additionally or alternatively, polymeric material 104 may be pre-fused to one or both fabric pieces 100 and/or 102, as described also later below with respect to FIGS. 16 and 17. The polymeric material 104 may optionally be provided at least on the face of the fabric 100 and/or 102 to be joined to the other component 100 and/or 102, whether or not the polymeric material 104 may also extend or penetrate through the fabric to its opposite face.

The polymeric material 104 may have a melting temperature that is lower than that at least one of the fabric pieces 100 and 102, optionally lower than that of both fabric pieces 100 and 102.

Upon heating, the polymeric material 104 melts and fuses to the respective fabric piece 100 or 102, or to the pieces 100 and 102 collectively. By performing the heating and/or welding at a temperature lower than the melting temperature of the fabric pieces 100 and 102, the integrity of the fibre(s) of the fabric pieces 100 and 102 can be preserved, thereby retaining the fabric strength even in the traditionally weak "heat affected zone" adjacent to a weld. Moreover, the polymeric material 104 may act as a filling material, flowing into the network of fibres to provide a strong mechanical bond with a large bond area, and providing an occlusive leak-free seal, for example at the interface between the fabric pieces 100 and 102. The heat may be introduced to the site, e.g. weld site, by any suitable technique, for example, by laser or by contact with a hot weld member or head, or by placing in a heated oven. In some embodiments, contact pressure applied to the or each fabric piece 100 and/or 102, or to the fabric pieces 100 and 102 collectively, may be generated by a heat-shrink material, in a manner similar to that already described above, or by application of external pressure (e.g. placing the fabric pieces in a vacuum or reduced pressure container).

In some embodiments, the fibres of the fabric may permit at least some reorientation of the fibre direction(s) away from the welded region, to permit the fabric to adapt to changes of size, for example, during crimping and expansion of the stent-valve, and/or during distension of the envelope of the skirt when the swellable material swells in use. For example, at least some (optionally at least a majority, optionally all or substantially all) of the fibres may be arranged obliquely (and/or non orthogonally) relative to a direction of the weld region, and/or relative to an axis of the stent-valve, and/or relative to a circumferential direction of the stent-valve.

Examples of biocompatible polymers that may be used as materials for the fabric pieces 100 and 102, and the polymeric material 104, are illustrated below in Table 1, together with an example melting temperature for each material (bearing in mind that when choosing a combination of materials, the polymeric material 104 may have a lower melting temperature than at least one, optionally both, of the fabric pieces 100 and 102, as already described).

TABLE 1

| Material | Available as fabric | Available as film and/or coating | Example Melting Temperature |
|---|---|---|---|
| Polyester (e.g. PET) | ✓ | ✓ | 250-260° C. |
| Polyether ether keeton (PEEK) | ✓ | ✓ | 340° C. |
| Polypropylene (PP) | ✓ | ✓ | 130° C. |
| Polytetrafluoroethylene (PTFE) | ✓ | ✓ | 325° C. |
| Polyurethanes (PU) family | not known | ✓ | 210-250° C. |
| Ultra-high molecular-weight polyethylene (UHMWPE) | ✓ | ✓ | not known |
| Silicone | not known | not known | not known |
| Polyacetal (POM) | ✓ | ✓ | 160-175° C. |
| Polyphenylsulfone (PPSU) | not known | ✓ | 370° C. |
| Polysulfone (PSU) | not known | ✓ | 180° C. |
| Polyvinylidene fluoride (PVDF) | ✓ | ✓ | 180° C. |
| Polyamide (PA) | ✓ | ✓ | 200-250° C. |

In one example, the fabric pieces 100 and 102 for the outer skirt may both be of PET, having a melting temperature of about 250° C., and the polymeric material 104 may be of polyurethane (PU) having a melting temperature around 210° C. The weld and/or fusing of the polymeric material, is performed at a temperature of at least 210° C., but less than 250° C.

During production of the skirt structures described herein, welding operations may be carried out with the swellable material 46 in situ. However, the inventors have appreciated that the swelling response of the material may be affected detrimentally by exposure to elevated temperatures. FIG. 13 shows how the swelling capacity (vertical axis) of an example hydrogel (at room temperature) is affected after exposure to heat at a range of temperatures (horizontal axis) simulated by 5 minutes heat in a temperature controlled oven. As may be seen in FIG. 13, the swelling capacity can be degraded by exposure to temperatures above about 150° C. The degradation is permanent, even when the hydrogel returns to room temperature. Since many of the welding temperatures discussed above exceed such temperature, there is a risk of a hydrogel being damaged by the manufacturing process unless care is taken. In some embodiments of the present disclosure, during the manufacture of the skirt, the swellable material 46 may be protected from excess temperatures. For example, cooling of the hydrogel or mandrel may be implemented, for example, by injecting cool air. A further possibility is to provide a mandrel with a heatsink arranged at a region in register with the position of the swellable material, to conduct heat away from that position. A further possibility is to provide a heat shield at the region desired to be protected, to reflect and/or diffuse applied heat energy (e.g. from a laser) to avoid excessive heating local to the heat shield.

Closely related to the above principles, instead of welding two fabrics together, the present disclosure also envisages a fabric (optionally a single piece), pores of the fabric being substantially occluded by a polymeric material. For example, the polymeric material may penetrate or impregnate the network of fibres of the fabric. Additionally or alternatively, the at least some of the polymeric material may be provided intra-fibre. The polymeric material may, for example, be a coating or a film on the fabric or a film fused with the fabric. In some embodiments, the fabric may be dip coated with the polymeric material.

In some embodiments, the polymeric material may, for example, be or comprise polyurethane. Additionally or alternatively, the fabric may optionally comprise PET.

In a closely related aspect, a method is disclosed comprising coating a fabric with a polymeric material to substantially occlude pores of the fabric with the polymeric material. The method may, for example, comprise dip coating the fabric with the polymeric material, or fusing or melting the polymeric material to the fabric, without substantially melting the fabric.

Use of such polymeric material may reinforce the fabric, and avoid risk of the pores enlarging uncontrollably if the fabric is subjected to stress that might otherwise cause the fabric to stretch and the pores to enlarge.

Optionally, in one or more regions of the fabric, the polymeric material provides (i) fusible material for welding to and/or welded to another piece or surface, and (ii) non-welded material that occludes pores of the fabric and/or reinforces the fabric. The polymeric material may be the same in both regions, e.g. polyurethane. Optionally, a further region of the fabric may have substantially open pores and/or substantially non-occluded pores, e.g. absent the polymeric material.

Figure 16:
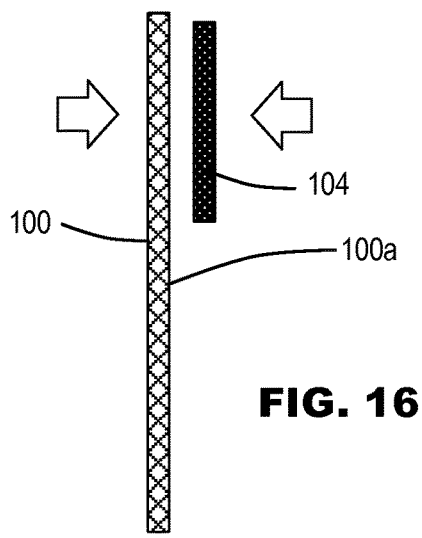
FIG. 16 is a schematic diagram illustrating a technique for fusing polymeric material to a fabric.
Figure 17:
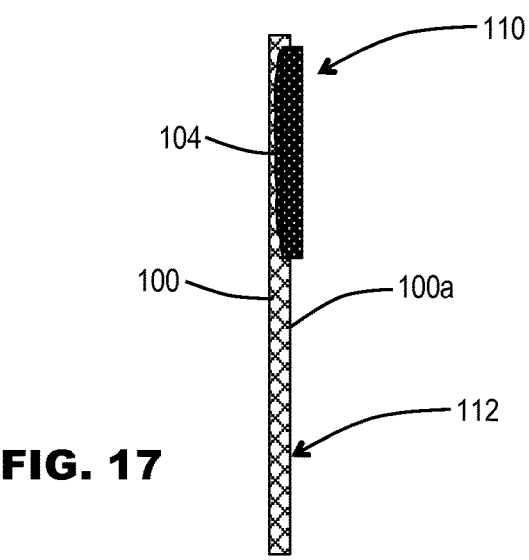
FIG. 17 is a schematic diagram illustrating the fabric of FIG. 16 after the fusing of the polymeric material.

FIGS. 16 and 17 illustrate an example of fusing polymeric material 104 to a fabric piece 100 (which may correspond to the fabric piece 100 and/or 102 described previously), to provide at least a fabric region 110 carrying the polymeric material 104, and optionally at least a fabric region 112 that is substantially absent the polymeric material 104. The fabric may be referred to as coated with polymeric material, at least in some region.

Referring to FIG. 16, the polymeric material 104 may be provided as a film. The polymeric material 104 may be provided in a pattern to match the desired pattern on the region(s) 110 of the fabric 100. For example, the polymeric material may be pre-cut or stamped in the desired pattern from sheet material and/or the polymeric material may be provided in strip form. In the illustrated form, the polymeric material 104 is provided on a first face 100a of the fabric 100, but polymeric material 104 may be provided on both faces, in the same or different patterns, as desired.

Heat may be applied to cause the polymeric material 104 to flow into, and/or fuse to, the fabric 100. The heat may be applied without substantially melting the fibers of the fabric 100. The heat may be applied by any suitable technique, for example, by laser or by contact with a hot weld member or head, or by placing in a heated oven. In some embodiments, contact pressure may be applied to urge the polymeric material 104 into intimate contact with the fabric 100, as illustrated by one or both of the arrows. Contact pressure may, for example, be applied by a heat-shrink material, in a manner similar to that already described above, or by application of external pressure (e.g. placing the fabric 100 and polymeric material 104 in a vacuum or reduced pressure container). In FIG. 16, contact pressure may be represented by the arrows.

Referring to FIG. 17, upon the cooling, a composite is produced comprising the fabric 100 having the polymeric material 104 fused thereto in one or more first regions 110, and optionally absent the polymeric material 104 in one or more second regions 112. The fabric may be referred to as coated with polymeric material (e.g. at least in some region). The polymeric material 104 may optionally provide a pad-like surface on the first face 100a of the fabric 100 corresponding to the face from which the polymeric material flows into the fabric. Depending on the process and materials used, in some embodiments, the polymeric material 104 may not penetrate completely through the fabric 100 to its opposite face. With such an arrangement, the polymeric material may behave like a plug that plugs or blocks the pores from one side. Alternatively, in some embodiments, polymeric material 104 may penetrate through the fabric to provide pad-like surfaces on both faces. Alternatively, polymeric material may, if desired, be provided to flow into the fabric from both faces, to form a block of polymeric material plugging the pores from both faces.

As described previously, in one or more regions 110 of the fabric, the polymeric material 104 provides (i) fusible material for welding to and/or welded to another piece or surface, and (ii) non-welded material that occludes pores of the fabric and/or reinforces the fabric. The polymeric material 104 may be the same in both regions 110, e.g. polyurethane. Optionally, a further region of the fabric 112 may have substantially open pores and/or substantially non-occluded pores, e.g. absent the polymeric material 104.

Figure 14:
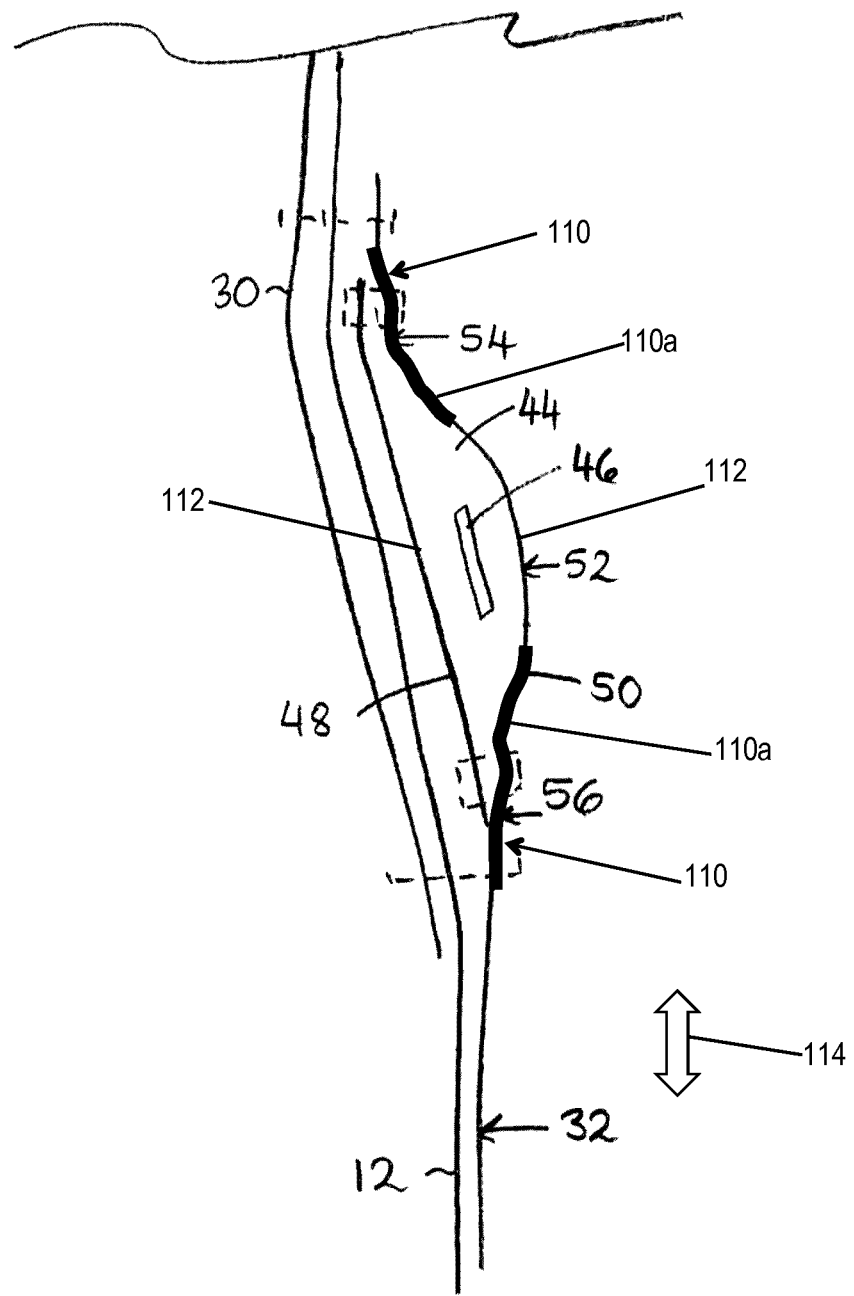
FIG. 14 is a schematic section through a further example of skirt structure similar to that of FIG. 11.

FIG. 14 illustrates, by way of example, a further embodiment of seal 40 incorporated within the outer skirt 32 of FIG. 1. The embodiment of FIG. 14 may be similar to that of FIG. 11. Optionally, the embodiment may include any one, or combination, or all of the details described above with respect to FIG. 2, except that the barrier wall portion 70 may be omitted. In particular, the seal of FIG. 14 may comprise the torroid envelope 42, swellable material 46, first (e.g. radially inner) wall portion 48, second (e.g. radially outer) wall portion 50. Either or both wall portions 48 and 50 may be of or comprise fabric as described previously. The outer wall portion 50 may optionally be thermoformed with an annular bulge shape. The wall portions 48 and 50 may be welded together at regions 54 and 56, e.g. by laser welding. The outer skirt may be sutured to the stent and/or inner skirt along suture lines above and below the envelope 42.

One or more regions 110 (indicated schematically by a thickened line) of at least one fabric piece wall portion 48 and/or 50 may be coated and/or covered with a polymeric material, for example, using any of the techniques mentioned above. In the illustrated example, regions 110 are provided in the second (e.g. radially outer) wall portion 50. The one or more regions 110 may cover substantially the entire area of the second wall portion 50, or only selected areas, for example, as illustrated in the drawing. A further region 112 may optionally be substantially uncovered or uncoated with such polymeric material, as may be the first (e.g radially inner) wall portion 48. Optionally the first wall portion 48 also has polymeric material coated in the regions corresponding to the position of the weld joint, to prime both wall portions 48 and 50 for a firm joint. In other examples, the first wall portion 48 may be completely uncoated with polymeric material. The polymeric material of the one or more regions 110 may provide two functions. Firstly, the polymeric material may provide a fusible material for forming the welded joints 54 and 56. Secondly, in areas 110a of the regions 110, the polymeric material (e.g. unwelded) may occlude the pores of the fabric material and/or reinforce the fabric material. The polymeric material may thereby avoid risk of the pores enlarging uncontrollably if the fabric is subjected to stress that might otherwise cause the fabric to stretch and the pores to enlarge. For example, such stress may occur if an attempt is made to recapture and/or resheath the prosthetic valve during an implantation procedure. Such recapture and/or resheathing may involve forcing a constraining sheath over the prosthesis, including the outer skirt, in an axial direction (indicated by either of arrow heads 114), to force the stent to collapse into the constraining sheath. In such case, the stress on the fabric material may be large, especially if the swellable material 46 has already started to swell and cause the seal to expand or distend. Stress-induced enlargement of the pores might lead to escape of the swellable material 46 by egress through the distorted fabric pores. As mentioned above, the polymeric material may avoid such risk, and thereby provide protection against accidental and undesired escape of the swellable material.

The regions 110 of the fabric may be rendered generally non-porous to liquids by the presence of the polymeric material occluding the fabric pores, at least for short durations. (E.g., without a diffusion barrier material, moisture may diffuse through the polymer material over an extended period of time). Blood or blood components may nevertheless enter the seal 40 by the one or more regions 112 that are not occluded by polymeric material.

Figure 15:
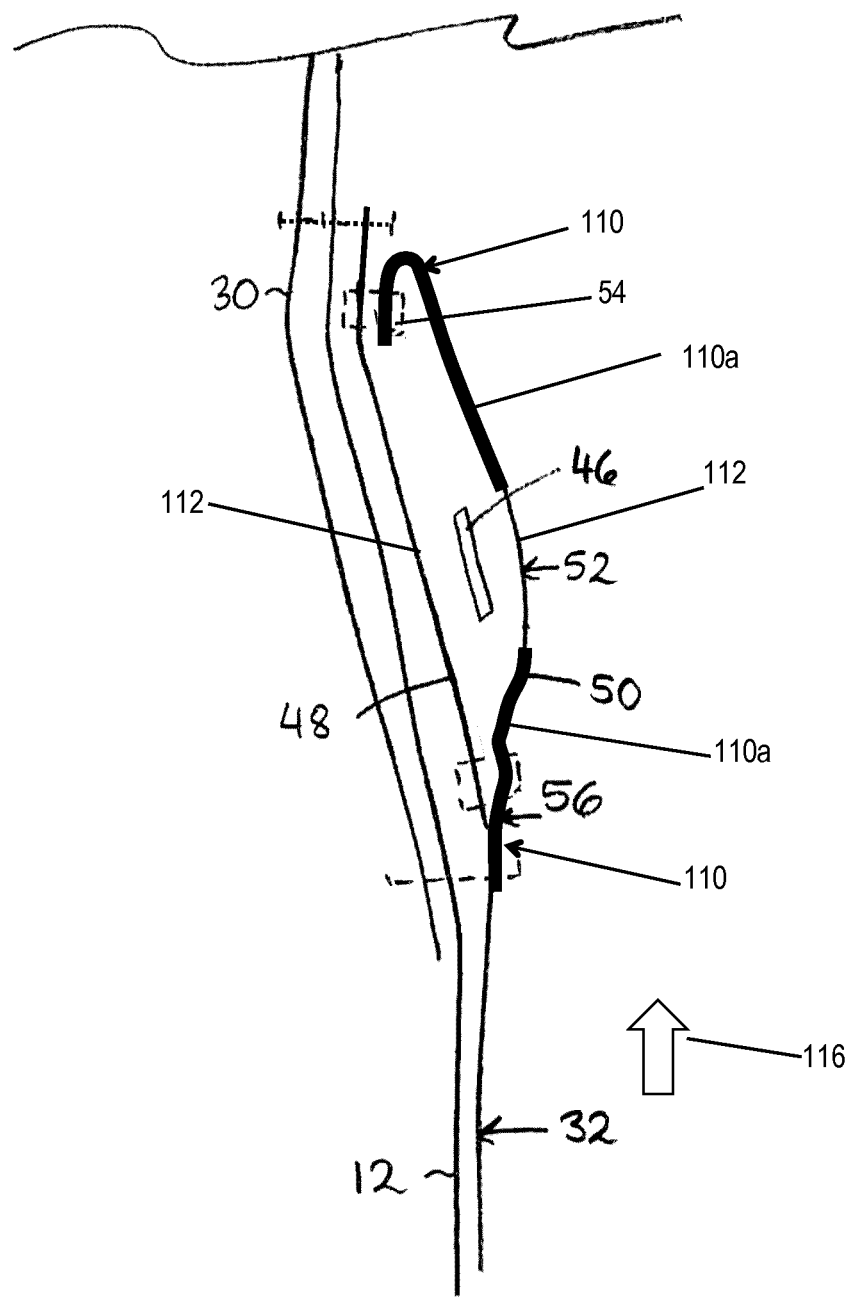
FIG. 15 is a schematic section through a further example of skirt structure similar to that of FIG. 14.

FIG. 15 shows a further embodiment, using similar principles to FIG. 14. This embodiment may include any of the features of FIG. 14. The principle difference in the embodiment of FIG. 15 is that the position of the upper suture to the stent and/or to the inner skirt, and the arrangement of the weld 54, may be modified. The second (e.g. radially outer) wall portion 50 may be turned back on itself like a folded cuff, and welded to the first (e.g. radially inner) wall portion 50 by a "hidden" or obscured weld 54. The first (e.g. radially inner) wall portion 48 may be extended upwardly above the weld 54, and be sutured to the stent 12 and/or to the inner skirt 30.

Such a modified form may be especially resistant to withstand recapture and/or resheathing forces applied if a constraining sheath is forced over the skirt in the direction 116. Even if the second (e.g. radially outer) wall portion 50 is folded, there is little bunching of material that could otherwise apply a force to the weld 54 in a "peeling" direction. The fabric may protect the integrity of the weld 54.

Figure 18:
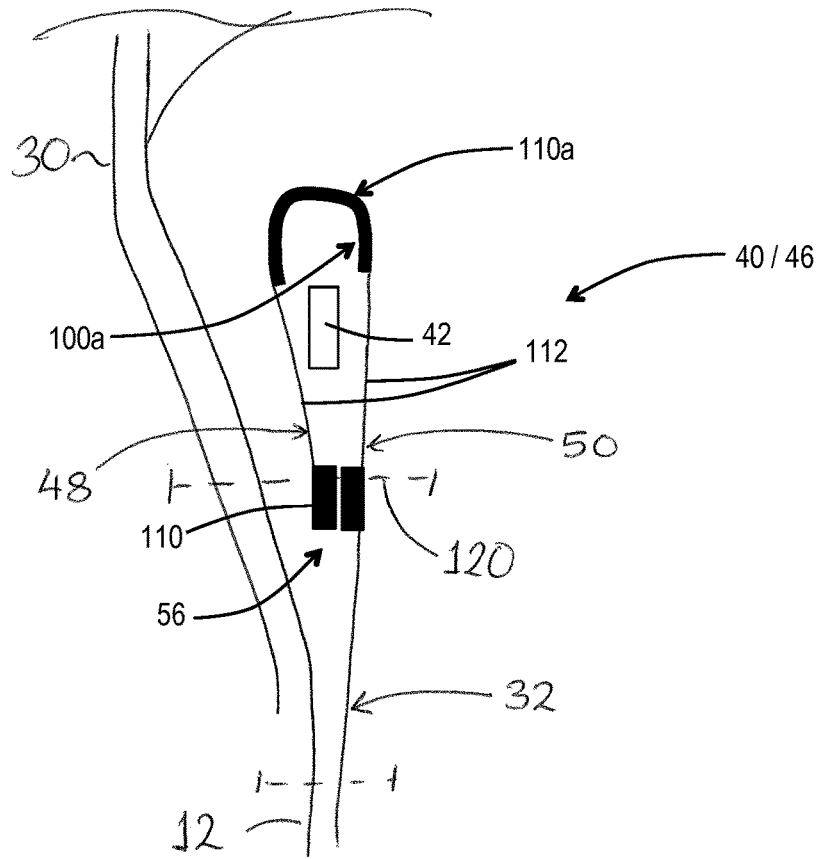
FIG. 18 is a schematic section through a further example of skirt structure similar to that of FIG. 2.

FIG. 18 shows a further embodiment of seal 40 incorporated, for example, within the outer skirt 32 of FIG. 1. The embodiment of FIG. 18 may include any one, or combination, or all of the details described above with respect to FIG. 2 and subsequent figures, except that the barrier wall portion 70 may optionally be omitted. In particular, the seal of FIG. 18 may comprise the torroid envelope 42, swellable material 46, first (e.g. radially inner) wall portion 48, second (e.g. radially outer) wall portion 50.

In the illustrated form, the wall portions 48 and 50 may be formed from a single piece of material folded to define the envelope 42. Such an arrangement may omit the upper join (e.g. weld) region 54 of preceding embodiments. Instead, the material may extend continuously integrally along a fold or bend, from the outer wall portion 50 to the inner wall portion 48. The lower edge of the inner wall portion 48 may be joined (e.g. welded) to the outer wall portion 50 to complete the envelope shape, by a join (e.g. weld) region 56 similar to that described previously. The join may be on a radially inwardly facing surface of the outer wall portion 50, thereby avoiding any exposed seams or join lines or other abrupt discontinuities on the exterior surface of the outer wall portion 50 that might complicate the ability (i) to slide the stent-valve axially through a compressing funnel for compressing or "crimping" the stent-valve, and/or (ii) to recapture the stent-valve into a catheter should this be desired during implantation. The second wall portion 50 may include the zig-zag skirt edge previously described (see FIG. 19).

The inner and outer wall portions 48 and 50 may be of, or comprise, fabric. The fabric may be coated and/or covered with polymeric material in one of more regions 110, optionally using the techniques described above. The polymeric material of the one or more regions 110 may provide two functions. Firstly, the polymeric material may provide a fusible material on one or both of the wall portions 48 and 50 for forming the welded joint(s) 56. Secondly, in one or more areas 110a of the regions 110, the polymeric material (e.g. unwelded) may occlude the pores of the fabric material and/or reinforce the fabric material. The polymeric material may thereby avoid risk of the pores enlarging uncontrollably if the fabric is subjected to stress that might otherwise cause the fabric to stretch and the pores to enlarge. For example, such stress may occur if an attempt is made to recapture and/or resheath the prosthetic valve during an implantation procedure, and/or during crimping of the prosthetic valve. For example, the area 110a may correspond to the fold or bend line or region at an upper extremity of the envelope 42.

In the present example, one or more of (e.g. at least some of) the areas 110 may optionally be provided from a face 100a of the fabric corresponding to an interior surface of the envelope 42. Such an arrangement may, for example, enhance the reinforcement and/or sealing of the fabric, plugging the fabric from the interior of the envelope 42, to resist outward egress of the swellable material through the pores. Additionally or alternatively, such an arrangement may reduce the quantity of polymeric material exposed on an exterior surface of the envelope, for example, a radially outwardly facing surface of the envelope 42, which might otherwise create a discontinuity or abrupt surface or a change in surface characteristic that might interfere with crimping and/or recapture of the prosthetic valve.

At least one of the inner and outer wall portions 48 and 50 may comprise one or more porous areas 112 that are not coated and/or not covered by polymeric material, and permit ingress of liquid (e.g. blood or a blood component) into the envelope to contact the swellable material. In the illustrated form, both the inner and outer wall portions 48 and 50 may each include a porous area 112. Alternatively, for example, the inner wall portion 48 may be substantially entirely coated and/or covered with polymeric material (not shown) so as to reinforce the inner wall portion 48 against undesired radially inward distension through the apertures of the stent when the swellable material expands.

In some embodiments, the single piece of material for the inner and outer wall portions 48 and 50 may be provided in an integral annular form without any axial join-line or seam, as described above. Alternatively, the outer skirt 32 may be formed from one or more sheets of material bent into a closed-loop and/or torroid shape, and secured together along a substantially axial join line. The join line may, for example, be formed by a weld, using fusible polymeric material, and optionally using the same weld techniques described above.

The skirt 32 may be sutured to the stent and/or inner skirt along one or more suture lines 120. The suture line 120 may optionally be below the envelope 42. If desired, the suture line 120 may be provided at the welded region 56.

Figure 19:
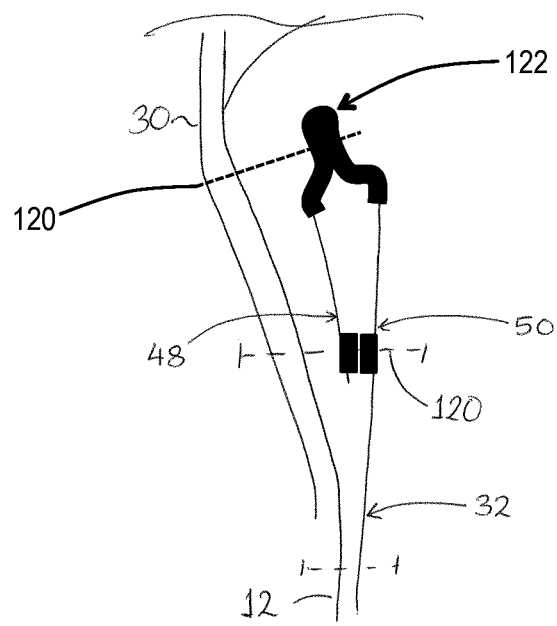
FIG. 19 is a schematic section through a further example of skirt structure similar to that of FIG. 18.

Referring to FIG. 19, if desired, one or more suture regions 122 may be provided in the bent or folded extremity of the envelope 42 (e.g. at the opposite extremity to the weld region 56). The suture region 122 may, for example, be provided by forming a pinched weld in the region 110 covered and/or coated with polymeric material. The pinched weld may be provided as a circumferentially continuous fin or flange of the envelope 42. Alternatively, the pinched weld may be provided in one or more circumferentially spaced regions, to define plural circumferentially spaced suture regions 122.

The suture regions 122 may be used to provide a further line of suture attachment to the stent, in a manner similar to that described previously.

Figure 20:
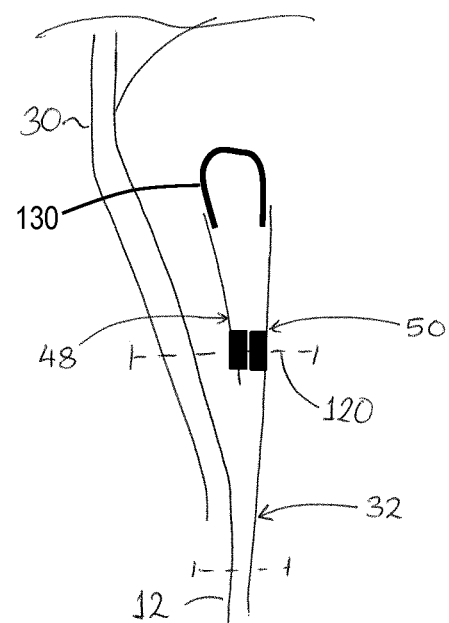
FIG. 20 is a schematic section through a further example of skirt structure similar to that of FIG. 18.

FIG. 20 illustrates a further example of skirt that is similar to the principles of FIG. 18 and may use any of the features of these embodiments, whether or not described explicitly below. In FIG. 20, the upper extremity of the envelope 42 is defined by a film 130 folded into an annular channel shape, and joined to inner and outer wall portions 48 and 50. The film 130 may be joined to the fabric by any suitable technique, e.g. by welding, and optionally using any of the weld techniques described above.

Figure 21:
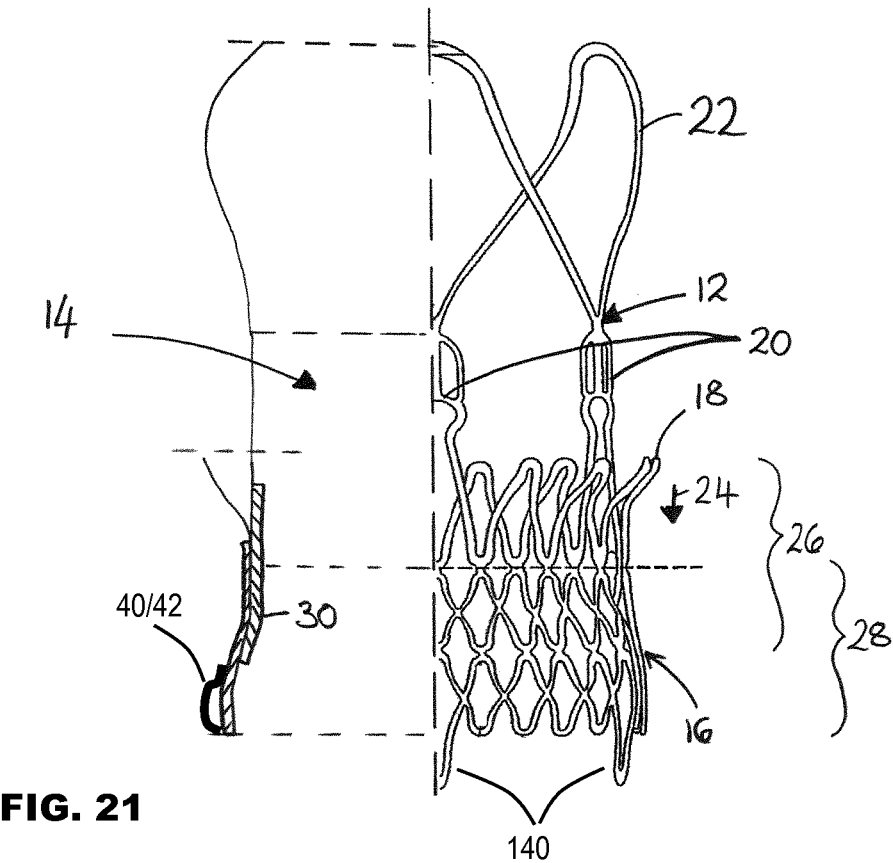
FIG. 21 is a schematic section, similar to FIG. 1, showing an alternative position of seal.
Figure 22:
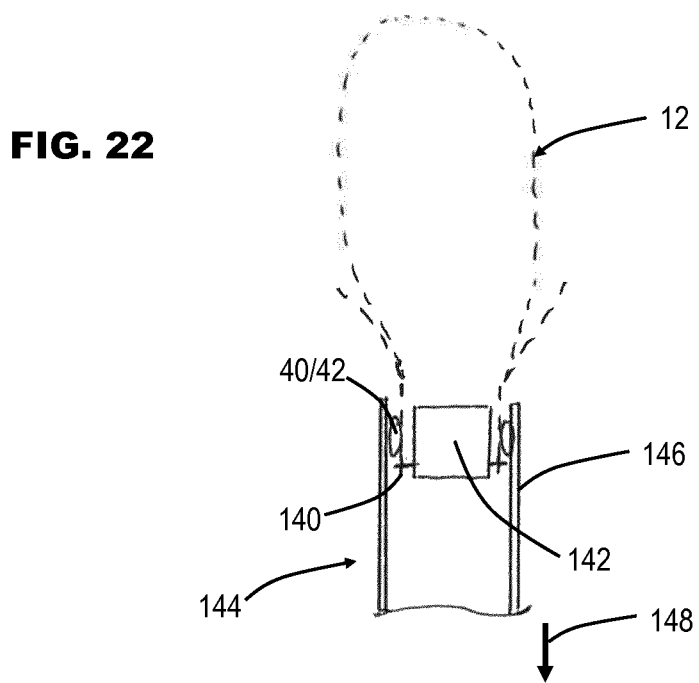
FIG. 22 is a schematic diagram illustrating implantation using a catheter sheath, shown in a partially deployed condition.

FIGS. 21 and 22 illustrate a further example of skirt that may optionally use any of the principles described above, whether or not described or shown explicitly. In FIG. 21, the envelope 42 (e.g. containing swellable material 46) is arranged to be adjacent to an end extremity of the stent 12. Optionally, the envelope 42 is arranged in a region adjacent to one or more attachment elements 140 for attaching the stent 12 to a stent holder 142 of a delivery catheter 144 (FIG. 22). The attachment elements 140 may, for example, comprise one or more eyes and/or apertures and/or extensions and/or hooks, for releasable engagement by complementary structure of the stent holder 142. The stent holder 142 may, for example, comprise male elements (e.g. projections and/or pins) and/or female elements (e.g. apertures and/or eyes and/or recesses and/or pockets) for engaging the attachment elements to form a releasable attachment. The attachment may self-detach or self-release, for example, when the stent 12 expands or is expanded, or the stent-holder 142 may be actuated to release engagement with the stent 12, for example, by displacement (e.g. retraction or withdrawal) of one or more locking components of the stent holder 142. The stent holder 142 may generally be a single-body, or it may comprise multiple bodies.

Whether or not the stent 12 comprises attachment elements 140, and/or whether or not the catheter 144 comprises a stent holder 142, the envelope may be arranged such that, in use, during displacement of a constraining sheath 146 to un-sheath the stent 12 (e.g. in the direction of arrow 148), the envelope 42 remains generally covered by the sheath 146 at least during initial unsheathing, optionally during a majority of the unsheathing. In some embodiments, the envelope 42 may be at a region of the stent that is a final region to be unsheathed, optionally with or just before unsheathing of attachment elements 140 (if provided). Such an arrangement can prevent swelling or expansion of the seal during initial progressive unsheathing, to allow the operator time to position the stent 12 for an optimum implantation. The seal may only be permitted to expand once the sheath 144 is moved to a fully open condition. If, during a partially unsheathed condition of the stent 12 as in FIG. 22, the operator desires to "re-capture" and/or "re-sheath" the stent (e.g. either to remove the stent 12 from the body, or to permit adjustment of the stent position at the implantation site), the operator may re-slide the sheath 146 over at least a portion of the stent 12 (e.g. in the opposite direction to arrow 148) to re-collapse the stent 12, e.g. at least partially, within the sheath 146. By not having unsheathed the envelope 42, the envelope 42 does not obstruct such re-sheathing and/or risk of damage to the envelope 42 can be reduced.

In a further related aspect, a composite material may be provided comprising a fabric and a polymeric material carried on, and/or coated on, and/or or impregnated in, and/or fused to, at least a first region of the fabric. In the first region, the composite material may combine some characteristics of a fabric, with some characteristics of a polymeric material. For example, like a fabric, the composite material may be suturable to other components, by passing suture thread through positions corresponding to pores of the fabric. The fibres of the fabric may provide a structural network or framework providing resistance to crack propagation from suture holes. Additionally or alternatively, like a polymeric material (e.g. film), the composite may bear stress without substantial pore enlargement. The polymeric material may reinforce the fabric material against pore enlargement; the fabric may reinforce the polymeric material against crack propagation. The composite material may be substantially flexible and/or thermo-formable. The composite material may be weldable and/or fusable and/or heat-sealable to other fabric and/or composite material.

The fabric may, for example, comprise PET. The polymeric material may, for example, comprise polyurethane.

Any other suitable materials, e.g. from the table above, may be substituted for the fabric and the polymeric material as desired.

It will be appreciate that the foregoing description is merely illustrative of exemplary forms of the disclosure, and that many modifications, equivalents and improvements may be made without departing from the scope and/or principles disclosed herein.

The invention claimed is:

1. A prosthetic cardiac valve comprising a fabric wall portion and a polymeric material fused to the fabric wall portion, the polymeric material having a melting temperature that is lower than that of the fabric wall portion, wherein axes of the fibres of the fabric are adapted to at least partially re-orient in a region away from the polymeric material, in response to changes in shape of the fabric.

2. The prosthetic valve of claim 1, wherein fibres of the fabric remain unmelted at an interface with the polymeric material, the polymeric material being attached to material to the fibres of the fabric wall portion by fusion.

3. The prosthetic valve of claim 1, further comprising a second fabric wall portion to which the polymeric material is fused.

4. The prosthetic valve of claim 3, wherein the polymeric material provides a welded joint between the fabric wall portions.

5. The prosthetic valve of claim 1, wherein the polymeric material substantially occludes pores of the fabric wall portion.

6. The prosthetic valve of claim 1, wherein the polymeric material does not extend substantially through the fabric wall portion.

7. The prosthetic valve of claim 1, wherein the polymeric material extends substantially through the fabric wall portion from one face to an opposite face.

8. The prosthetic valve of claim 1, wherein the fabric comprises one or more first regions provided with polymeric material fused to the fabric wall portion, and one of more second regions absent said polymeric material.

9. The prosthetic valve of claim 1, comprising at least one welded region in which polymeric material is fused to first and second fabric wall portions to provide a joint between the wall portion, and at least one non-welded region in which polymeric material is fused to only a single fabric wall portion.

10. The prosthetic valve of claim 1, wherein the fabric is a woven fabric.

11. The prosthetic valve of claim 1, wherein at least one of the fabric wall portion and the polymeric material is selected from the group consisting of: polyester; polyethylene terephthalate (PET); polyether ether ketone (PEEK); polypropylene (PP); polytetrafluroethylene (PTFE); polyurethane (PU); ultra-high molecular weight polyethylene (UHMWPE); silicone; polyacetal; polyphenylsulfone; polysulfone; polyvinylidene fluoride; polyamide.

12. The prosthetic valve of claim 11, wherein the fabric wall portion comprises polyester (e.g. PET), and the polymeric material comprises polyurethane.

13. The prosthetic valve of claim 1, further comprising a stent component and a skirt carried by the stent component, wherein the skirt comprises the fabric wall portion.

14. The prosthetic valve of claim 13, wherein the skirt does not have a peelable cover.

15. The prosthetic valve of claim 14, wherein the skirt defines an envelope containing a material that swells when contact by blood or a blood component.

* * * * *